US012636485B2

(12) United States Patent
Ryan et al.

(10) Patent No.: US 12,636,485 B2
(45) Date of Patent: May 26, 2026

(54) CATHETER BLOOD PUMPS

(71) Applicant: Shifamed Holdings, LLC, Campbell, CA (US)

(72) Inventors: Ari Ryan, San Jose, CA (US); Crissly Crisostomo, Campbell, CA (US); Shayan Assani, Sunnyvale, CA (US); Daniel Varghai, Scotts Valley, CA (US); Ha Luong, San Jose, CA (US)

(73) Assignee: Shifamed Holdings, LLC, Santa Clara, CA (US)

( * ) Notice: Subject to any disclaimer, the term of this patent is extended or adjusted under 35 U.S.C. 154(b) by 301 days.

(21) Appl. No.: 18/552,430

(22) PCT Filed: Mar. 24, 2022

(86) PCT No.: PCT/US2022/021740
§ 371 (c)(1),
(2) Date: Sep. 25, 2023

(87) PCT Pub. No.: WO2022/204400
PCT Pub. Date: Sep. 29, 2022

(65) Prior Publication Data
US 2024/0157117 A1     May 16, 2024

Related U.S. Application Data

(60) Provisional application No. 63/165,222, filed on Mar. 24, 2021.

(51) Int. Cl.
*A61M 1/10*        (2006.01)
*A61M 1/12*        (2006.01)
(Continued)

(52) U.S. Cl.
CPC .......... *A61M 60/808* (2021.01); *A61M 60/13* (2021.01); *A61M 60/237* (2021.01);
(Continued)

(58) Field of Classification Search
CPC .......... A61M 2207/00; A61M 2230/30; A61M 60/13; A61M 60/139; A61M 60/174;
(Continued)

(56) References Cited

U.S. PATENT DOCUMENTS 4,625,712 A    12/1986  Wampler
4,753,221 A     6/1988  Kensey et al.
(Continued)

FOREIGN PATENT DOCUMENTS

CA        3014105 A1    8/2017
EP        3131599 A1    2/2017
(Continued)

*Primary Examiner* — Jon Eric C Morales
(74) *Attorney, Agent, or Firm* — Shay Glenn LLP

(57)     ABSTRACT

Catheter blood pumps that include an expandable pump portion. The pump portions include a collapsible blood conduit that defines a blood lumen. The collapsible blood conduits include a collapsible scaffold adapted to provide radial support to the blood conduit. The pump portion also includes one or more impellers. The collapsible scaffold and/or an elongate member extending proximally from the pump portion may include portions of differing radial stiffness or flexibility.

21 Claims, 23 Drawing Sheets

(51) Int. Cl.

| | |
|---|---|
| *A61M 60/13* | (2021.01) |
| *A61M 60/237* | (2021.01) |
| *A61M 60/414* | (2021.01) |
| *A61M 60/808* | (2021.01) |
| *A61M 60/825* | (2021.01) |
| *A61M 60/857* | (2021.01) |

(52) U.S. Cl.
CPC ........ *A61M 60/414* (2021.01); *A61M 60/825* (2021.01); *A61M 60/857* (2021.01)

(58) Field of Classification Search
CPC .............. A61M 60/216; A61M 60/237; A61M 60/295; A61M 60/414; A61M 60/808; A61M 60/81; A61M 60/816; A61M 60/857; A61M 60/865
See application file for complete search history.

(56) References Cited

U.S. PATENT DOCUMENTS

| | | | |
|---|---|---|---|
| 5,061,256 | A | 10/1991 | Wampler |
| 5,287,858 | A | 2/1994 | Hammerslag et al. |
| 5,507,629 | A | 4/1996 | Jarvik |
| 5,735,892 | A | 4/1998 | Myers et al. |
| 6,007,478 | A | 12/1999 | Siess et al. |
| 6,053,943 | A | 4/2000 | Edwin et al. |
| 6,685,696 | B2 | 2/2004 | Fleischhacker et al. |
| 6,712,844 | B2 | 3/2004 | Pacetti |
| 7,022,100 | B1 | 4/2006 | Aboul Hosn et al. |
| 7,027,875 | B2 | 4/2006 | Siess et al. |
| 7,220,275 | B2 | 5/2007 | Davidson et al. |
| 7,828,710 | B2 | 11/2010 | Shifflette |
| 8,388,565 | B2 | 3/2013 | Shifflette |
| 8,485,961 | B2 | 7/2013 | Campbell et al. |
| 8,535,211 | B2 | 9/2013 | Campbell et al. |
| 8,591,393 | B2 | 11/2013 | Walters et al. |
| 8,597,170 | B2 | 12/2013 | Walters et al. |
| 8,721,517 | B2 | 5/2014 | Zeng et al. |
| 8,734,508 | B2 | 5/2014 | Hastings et al. |
| 8,814,776 | B2 | 8/2014 | Hastie et al. |
| 8,814,933 | B2 | 8/2014 | Siess |
| 8,849,398 | B2 | 9/2014 | Evans |
| 8,932,141 | B2 | 1/2015 | Liebing |
| 8,934,956 | B2 | 1/2015 | Glenn et al. |
| 9,028,216 | B2 | 5/2015 | Schumacher et al. |
| 9,028,392 | B2 | 5/2015 | Shifflette |
| 9,072,825 | B2 | 7/2015 | Pfeffer et al. |
| 9,138,518 | B2 | 9/2015 | Campbell et al. |
| 9,180,235 | B2 | 11/2015 | Forsell |
| 9,446,179 | B2 | 9/2016 | Keenan et al. |
| 9,512,839 | B2 | 12/2016 | Liebing |
| 9,833,550 | B2 | 12/2017 | Siess |
| 9,872,948 | B2 | 1/2018 | Siess |
| 10,052,419 | B2 | 8/2018 | Er |
| 10,208,763 | B2 | 2/2019 | Schumacher et al. |
| 10,357,598 | B2 | 7/2019 | Aboul-Hosn et al. |
| 10,881,770 | B2 | 1/2021 | Tuval et al. |
| 10,894,115 | B2 | 1/2021 | Pfeffer et al. |
| 11,185,677 | B2 | 11/2021 | Salahieh et al. |
| 11,268,521 | B2 | 3/2022 | Toellner |
| 11,280,345 | B2 | 3/2022 | Bredenbreuker et al. |
| 11,850,413 | B2 | 12/2023 | Zeng et al. |
| 12,017,056 | B2 | 6/2024 | Guo et al. |
| 2005/0277803 | A1 | 12/2005 | Pecor |
| 2007/0250148 | A1 | 10/2007 | Perry et al. |
| 2009/0082723 | A1 | 3/2009 | Krogh et al. |
| 2014/0148638 | A1 | 5/2014 | LaRose et al. |
| 2015/0238671 | A1 | 8/2015 | Mesallum |
| 2015/0328382 | A1 | 11/2015 | Corbett et al. |
| 2016/0022890 | A1 | 1/2016 | Schwammenthal et al. |
| 2016/0053763 | A1 | 2/2016 | Toellner |
| 2017/0014562 | A1 | 1/2017 | Liebing |
| 2017/0037860 | A1 | 2/2017 | Toellner |
| 2017/0100527 | A1 | 4/2017 | Schwammenthal et al. |
| 2017/0173242 | A1 | 6/2017 | Anderson et al. |
| 2017/0232169 | A1 | 8/2017 | Muller |
| 2017/0340788 | A1 | 11/2017 | Korakianitis et al. |
| 2018/0080326 | A1 | 3/2018 | Schumacher et al. |
| 2018/0149164 | A1 | 5/2018 | Siess |
| 2018/0303990 | A1 | 10/2018 | Siess et al. |
| 2020/0121835 | A1 | 4/2020 | Farago et al. |
| 2020/0237981 | A1 | 7/2020 | Tuval et al. |
| 2020/0316268 | A1 | 10/2020 | Antoni et al. |
| 2021/0008261 | A1* | 1/2021 | Calomeni ........... A61M 60/139 |
| 2022/0203084 | A1 | 6/2022 | Zarins et al. |

FOREIGN PATENT DOCUMENTS

| | | |
|---|---|---|
| EP | 3153190 A1 | 4/2017 |
| EP | 3000493 B1 | 5/2017 |
| WO | WO01/019444 A1 | 3/2001 |
| WO | WO2015/177793 A2 | 11/2015 |
| WO | WO2018/061002 A1 | 4/2018 |
| WO | WO2018/067410 A1 | 4/2018 |
| WO | WO2018/078615 A1 | 5/2018 |
| WO | WO2018/088939 A1 | 5/2018 |
| WO | WO2018/089970 A1 | 5/2018 |
| WO | WO2018/096531 A1 | 5/2018 |
| WO | WO2019/191851 A1 | 9/2019 |
| WO | WO2019/194956 A1 | 10/2019 |

* cited by examiner different pitch than

AA

LV

AV

320

CATHETER BLOOD PUMPS

CROSS REFERENCE TO RELATED APPLICATIONS

This application claims the benefit of U.S. Application No. 63/165,222, filed Mar. 24, 2021 which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

The disclosure is related to intravascular blood pump and their methods of and manufacture.

In some embodiments, a catheter blood pump (e.g., 2800) is provided, comprising: a pump portion (e. g., 2810) comprising an inflow, a blood conduit, an outflow, and an impeller disposed at least partially within the blood conduit; an elongate body (e.g., 2820) coupled to and extending proximally from the pump portion, wherein a distal region of the elongate body includes a preferential bending region (e.g., 2830) that is more flexible than a first region (e.g., 2850) of the elongate body adjacent to and proximal to the preferential bending region and more flexible than a second region (e.g., 2860) of the elongate body adjacent to and distal to the preferential bending region, the second region (e.g., 2860) adjacent to and proximal to the outflow of the pump.

In some embodiments, the preferential bending region is more flexible than the outflow region of the pump portion.

In some embodiments, the preferential bending region includes at least one of material or structure that contributes at least partially to the relatively greater flexibility in the preferential bending region.

In other embodiments, the preferential bending region has a flexibility such that when the pump portion is positioned across an aortic valve, the preferential bending region assumes a bent configuration in an ascending aorta so as to maintain as co-linear an impeller long axis and a blood conduit long axis at the location of the impeller.

In additional embodiments, a proximal end of the impeller, including a blade, is only partially covered by the blood conduit.

In some embodiments, the first region (e.g., 2850) includes a distal end of an elongate outer catheter shaft (e.g., 2840).

In some embodiments, the first region includes a distal end of drive cable tube (e.g., 2882), the drive cable tube extending around a drive cable (e.g., 2880).

In additional embodiments, the first region includes a distal end of the drive cable tube.

In various embodiments, the first region includes a clean fluid path and a fluid return pathway (e.g., "F").

In other embodiments, the preferential bending region includes a clean fluid pathway (e.g., "F").

In some embodiments, the second region (e.g., 2860) comprises a bearing housing (e.g., 2861) that houses at least one bearing (e.g., 2862).

In some embodiments, the bearing housing is a proximal bearing housing, the catheter blood pump further comprising a distal bearing housing disposed distal to a distal end of the blood conduit (examples of which are provided in this disclosure).

In various embodiments, the second region (e.g., 2860) that is distal to the preferential bending region comprises a rigid cylindrical member (e.g., 2861) disposed about a bearing (e.g., 2862).

In additional embodiments, the preferential bending region has a length from 0.5 inches to 7 inches, optionally from 1 inch-5 inches.

In various embodiments, the preferential bending region comprises a flexible tubular member (e.g., 2831) with a plurality of gaps formed through the flexible tubular member, the plurality of gaps at least partially contributing to the flexibility of the flexible region.

In some embodiments, the plurality of gaps are part of a continuous gap formed in the flexible tubular member.

In some embodiments, the continuous gap includes at least a section with a helical configuration.

In additional embodiments, the plurality of gaps are formed by a plurality of interlocking structural elements.

In other embodiments, the plurality of interlocking structural elements are spaced so as to allow for some axial movement therebetween and further prevent axial movement therebetween beyond a certain amount.

In some embodiments, the plurality of interlocking structural elements are spaced so as to allow for some rotational movement therebetween and further prevent circumferential movement therebetween beyond a certain amount.

In some embodiments, the plurality of gaps (optionally formed by laser cutting a tube) are sized, configured and positioned to facilitate and allow collapse of the pump portion within at most a 10 F sheath in response to a distal sheathing force on the pump portion, wherein the distal sheathing force creates tension in the preferential bending region.

In some embodiments, the tension in the flexible region in response to the sheathing force causes the plurality of gaps to increase in size in an axial dimension.

In some embodiments, the preferential bending region includes axial travel limiters (optionally based on a cut pattern of the flexible tubular member (e.g., 2831) that are sized and configured to limit the distal travel between adjacent surfaces of the flexible tubular member, optionally in response to the tension created in the flexible region.

In additional embodiments, the plurality of gaps comprise a single continuous gap, optionally with at least partially helical configuration in the flexible tubular member.

In various embodiments, the plurality of gaps comprise a plurality of axially spaced discontinuous gaps in the flexible tubular member, optionally with solid tubular sections therebetween.

In some embodiments, the plurality of gaps have a non-constant pattern along at least a portion of length of the flexible tubular member.

In some embodiments, the non-constant pattern imparts a variable flexibility along the length of the flexible tubular member.

In additional embodiments, the plurality of gaps have a constant pattern along at least a portion of the flexible tubular member.

In some embodiments, a flexible coating is disposed about (optionally directly about) the flexible tubular member (e.g., 1831), the flexible coating extending over the plurality of gaps and optionally creating a fluid tight seal.

In some embodiments, the flexible tubular member at least partially defines a fluid pathway (e.g., "F").

In some embodiments, the elongate body comprises an elongate catheter shaft (e.g., 2840, optionally comprising an elastomeric material) with a distal end that does not extend into the preferential bending region but is coupled thereto, the elongate catheter shaft having a larger outer diameter than an outer diameter of the preferential bending region.

In additional embodiments, the preferential bending region includes a flexible tubular member (e.g., 2831) that comprises stainless steel.

In some embodiments, the preferential bending region includes a flexible tubular member (e.g., 2831) with a plurality of gaps therein, wherein the flexible tubular member comprises a material such that the flexible tubular member would be less flexible if it did not include any gaps therein.

In some embodiments, the preferential bending region comprises a pattern such that a distal end of the preferential bending region is adapted to rotate relative to a proximal end of the preferential bending region in response to a twisting force on the distal end of the preferential bending region when the proximal end of the preferential bending region is held stationary.

In other embodiments, the preferential bending region has variable flexibility along its length.

In some embodiments, a proximal region (e.g., 2832, 2932) of the preferential bending region is less flexible than a central region (e.g., 2834, 2934) of the preferential bending region, the proximal region being a flexibility transition region between a catheter shaft distal end and the central region of the preferential bending region.

A catheter blood pump is provided, comprising: a pump portion comprising an inflow, a blood conduit, an outflow, and one or more impellers disposed at least partially within the blood conduit; an elongate body (e.g., 2820) coupled to and extending proximally from the pump portion (e.g., 2810), wherein a distal region of the elongate body includes a preferential bending region (e.g., 2830) with a flexibility such that, in response to a lateral load applied to a distal end of the preferential bending region or to the pump portion, the preferential bending portion bends and maintain as co-linear an impeller long axis and a pump portion long axis at the location of the impeller, the impeller disposed in a proximal region of the pump portion.

A catheter blood pump is provided, comprising: a pump portion comprising an inflow, a blood conduit, an outflow, a proximal impeller disposed in a proximal portion of the blood conduit and a distal impeller disposed in a distal portion of the blood conduit; an elongate body (e.g., 2820) coupled to and extending proximally from the pump portion (e.g., 2810), a distal region of the elongate body including a flexible preferential bending region (e.g., 2830), wherein the flexible preferential bending region is spaced proximally from the pump portion and has a length such that the flexibility of the flexible preferential bending region at least contributes to maintaining as co-linear a long axis of the proximal impeller and the pump portion at the location of the proximal impeller.

A catheter blood pump (e.g., 2800) is provided, comprising: a pump portion (e.g., 2810) comprising an inflow, a blood conduit, an outflow, and one or more impellers disposed at least partially within the blood conduit; an elongate body (e.g., 2820) coupled to and extending proximally from the pump portion, wherein a flexible preferential bending region of the elongate body has a flexibility such that, when the catheter blood pump is held horizontally in a fixture at a sheath (e.g., 2890) distal end when the sheath is in a retracted position, a greatest amount of bend in the elongate body or pump portion distal to where the blood pump is held in the fixture is in the preferential bending region (e.g., 2830) of the elongate body.

A catheter blood pump is provided, comprising: a pump portion (e.g., 2810) comprising an inflow, a blood conduit, an outflow, and one or more impellers disposed at least partially within the blood conduit; an elongate body (e.g., 2820) coupled to and extending proximally from the pump portion, wherein a flexible distal region of the elongate body includes a preferential bending portion (2830) with a flexibility such that, when a blood conduit of the pump portion is placed across an aortic valve with a distal end of the pump portion in a left ventricle and the distal region of the elongate body disposed in an ascending aorta, the flexible preferential bending portion is adapted to assume a bent configuration with a degree of bend greater than any portion of the blood conduit.

A method of positioning a catheter blood pump is provided, comprising:

positioning a pump portion across an aortic valve, an elongate body coupled to the pump portion and extending proximally therefrom; and withdrawing a sheath distal end proximally from a positioning distal to a preferential bending region of the elongate body to a position proximal to the preferential bending region to expose the preferential bending region and allow the preferential bending region to assume a bent configuration in an aorta.

In some embodiments, a distal region (e.g., 2836, 2936) of the preferential bending region is less flexible than a central region (e.g., 2834, 2934) of the preferential bending region, the distal region being a flexibility transition region between the central region of the preferential bending region and a stiffer distal region of the elongate body (e.g., 2860).

In some embodiments, the preferential bending region includes a central region, a distal flexibility transition region with increasing stiffness in the distal direction, and a proximal flexibility transition region with increasing stiffness in the proximal direction.

In various embodiments, the distal flexibility transition region has a length that is less than a length of the proximal flexibility transition region.

In some embodiments, the central region is longer than the distal and proximal flexibility transitions regions.

In other embodiments, the preferential bending zone includes a plurality of gaps therein, and wherein a pitch angle in the central region is less than a pitch angle in the distal flexibility transition region and a pitch angle in the proximal flexibility transition region.

In some embodiments, the distal flexibility transition region includes a plurality of regions having different flexibility.

In some embodiments, the proximal flexibility transition region includes a plurality of regions having different flexibility.

A catheter blood pump (e.g., 2800) is provided, comprising: a pump portion (e. g., 2810) comprising an inflow, a blood conduit, an outflow, and a proximal impeller disposed at least partially within a proximal region of the blood conduit; an elongate body (e.g., 2820) coupled to and extending proximally from the pump portion, wherein the elongate body includes a preferential bending region (e.g., 2830) adjacent to the proximal region of the blood conduit that is more flexible than a first region (e.g., 2850) of the elongate body adjacent to and proximal to the preferential bending region and more flexible than the proximal region of the blood conduit.

In some embodiments, the blood conduit further comprises a central region and a distal region, wherein the central region is more flexible than the proximal region of the blood conduit.

In some embodiments, the distal region of the blood conduit is stiffer than the central region of the blood conduit.

DETAILED DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
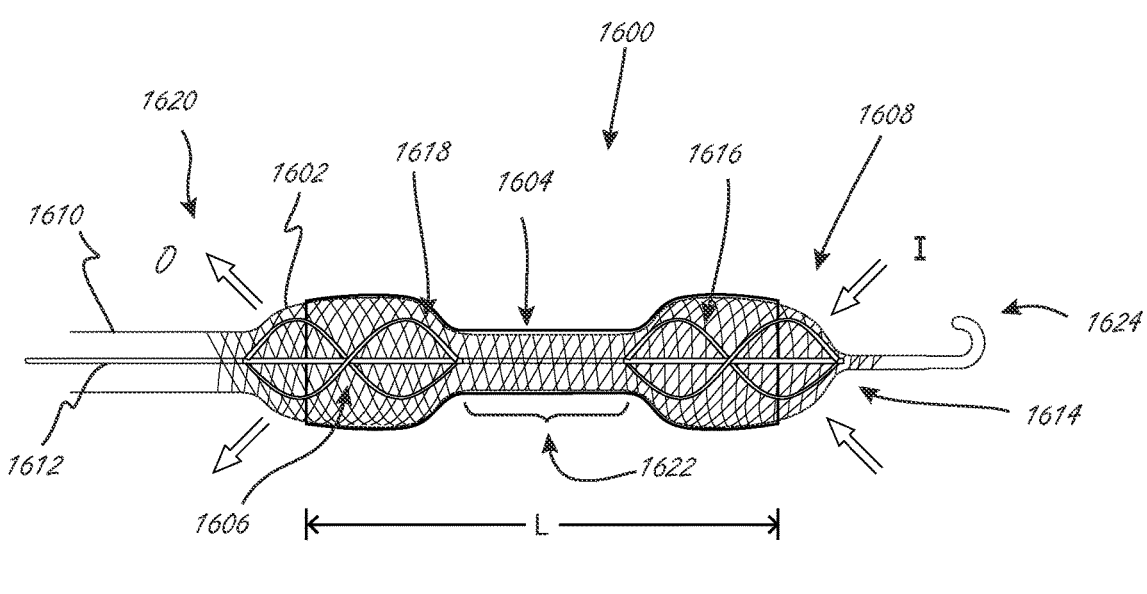
FIG. 1 is a side view of an exemplary expandable pump portion that includes an expandable impeller housing that includes a scaffold and blood conduit, and a plurality of impellers.

FIG. 1 is a side view illustrating a distal portion of an exemplary catheter blood pump, including pump portion 1600, wherein pump portion 1600 includes proximal impeller 1606 and (optional) distal impeller 1616, both of which are in operable communication with drive cable 1612. Pump portion 1600 is in an expanded configuration in FIG. 1, but is adapted to be collapsed to a delivery configuration so that it can be delivered with a lower profile. The impeller(s) can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to herein as expandable scaffolds or scaffold sections. Expandable scaffold 1602 is disposed radially outside of the impellers along the axial length of the impellers. Expandable scaffold 1602 can be constructed in a manner and made from materials similar to many types of expandable structures that are known in the medical arts to be able to collapsed and expanded, examples of which are provided herein. Examples of suitable materials include, but are not limited to, polyurethane, polyurethane elastomers, metallic alloys, etc.

Pump portion 1600 also includes blood conduit 1604, which is coupled to and supported by expandable member 1602, has a length L, and extends axially between the impellers. Conduit 1604 creates and provides a fluid lumen between the two impellers. When in use, fluid moves through the lumen defined by conduit 1604. The conduits herein may be non-permeable, or they may be semi-permeable, or even porous as long as they still define a lumen. The conduits herein are also flexible, unless otherwise indicated. The conduits herein extend completely around (i.e., 360 degrees) at least a portion of the pump portion. In pump portion 1600, the conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to pump portions without a conduit. As described herein, expandable members or scaffolds may also be considered to be a part of the blood conduit generally, which together define a blood lumen. In these instances the scaffold and material supported by the scaffold may be referred to herein as an expandable impeller housing or housing.

Expandable member 1602 may have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24 F (4.0-8.0 mm) where the impellers are axially within the expandable member, and to an outermost dimension of 10-20 F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 can have an outer configuration that tapers as it transitions from the impeller regions to central region 1622, and again tapers at the distal and proximal ends of expandable member 1602. In other embodiments, the expandable member 1602 can have a generally uniform diameter or thickness in the expanded configuration.

The expandable member 1602 can have sections of varying stiffness or flexibility. For example, one or more impeller regions of the expandable member 1602, such as the regions surrounding proximal impeller 1606 and/or distal impeller 1616, can have increased stiffness relative to the central region 1622. In some embodiments, as described above, the expandable member 1602 includes only a proximal impeller 1606, and no distal impeller 1616. However, even in embodiments with only a single impeller, such as proximal impeller 1606, the distal and proximal sections or regions of the expandable member may still be more stiff than the central region 1622. The central region can include more flexibility so as to facilitate placement across a valve.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superplastic wire frame, with polymer or other material that acts as a webbing across the wire frame, such as those described in U.S. Pat. No. 6,533,716, the disclosure of which is incorporated by reference herein for all purposes. Although the embodiment of FIG. 1 is shown with two impellers, proximal impeller 1606 and distal impeller 1616, it should be understood that other embodiments can include only a single impeller, such as proximal impeller 1606, and no distal impeller.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or U.S. Pat. No. 8,052,749, the disclosures of which are incorporated by reference herein.

Figure 2:
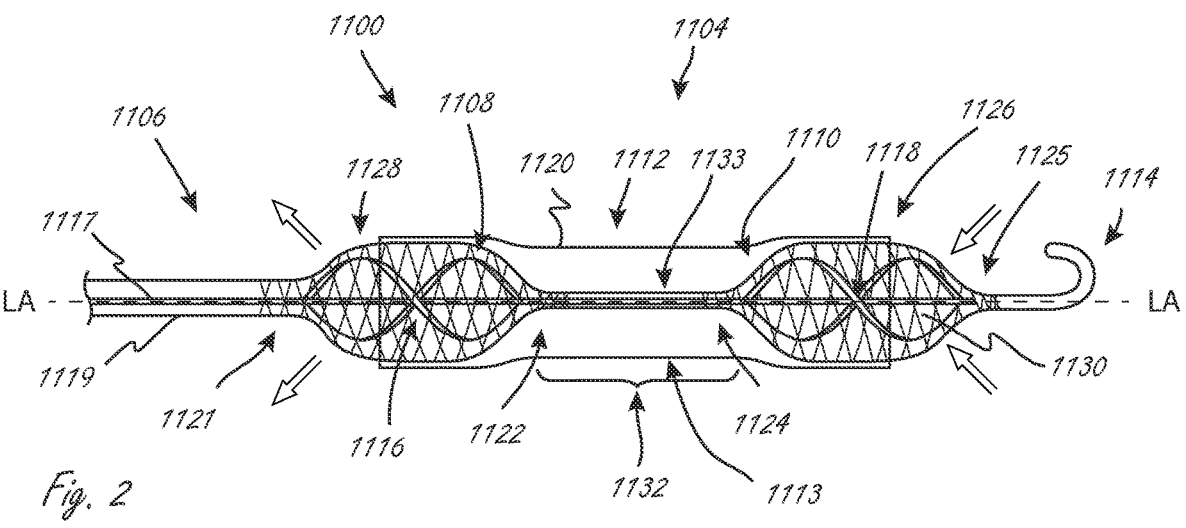
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. Nos. 7,841,976 or 8,052,749, the disclosures of which are incorporated by reference herein for all purposes.

Figures 3A, 3B:
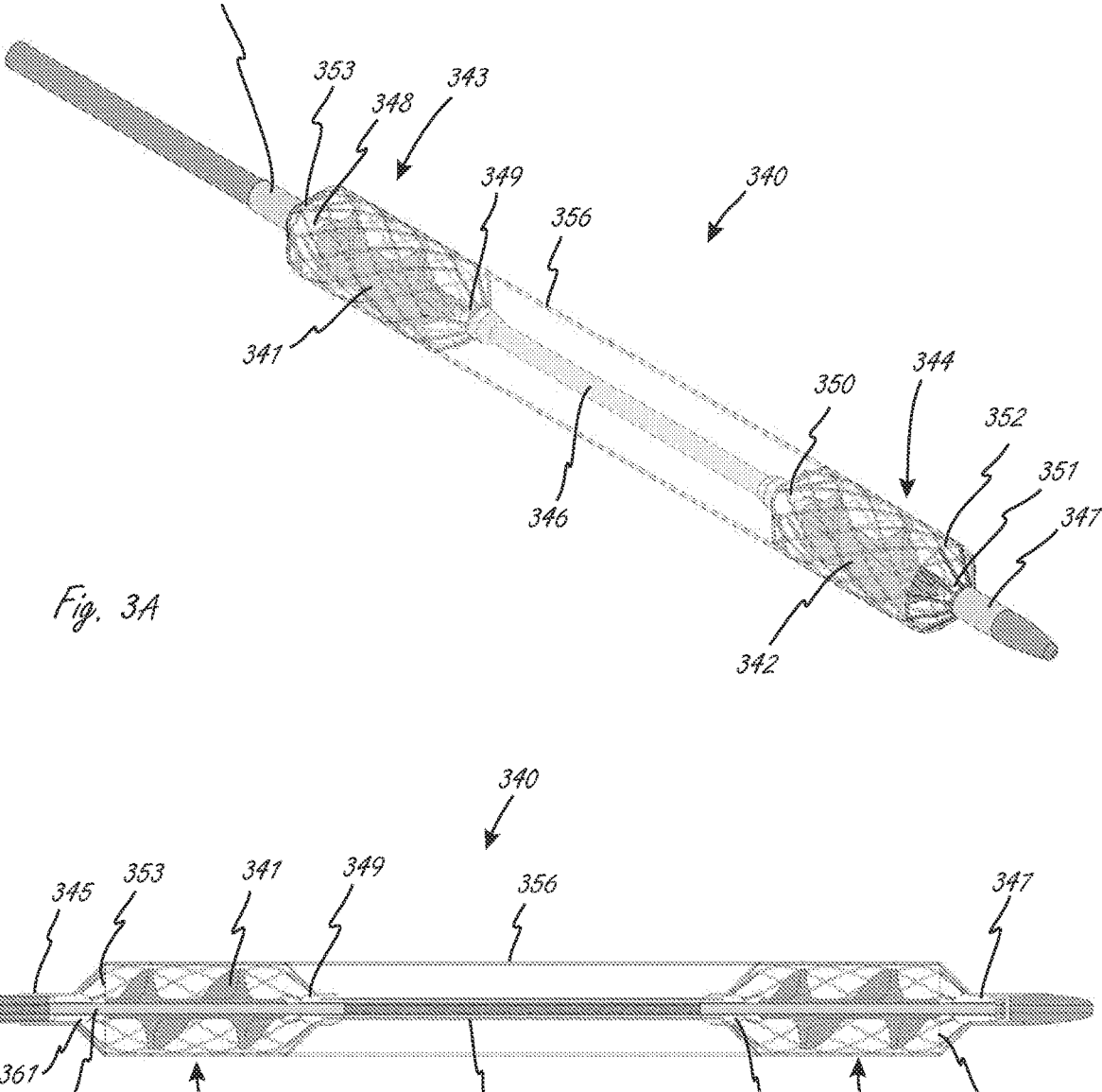
FIGS. 3A, 3B, 3C and 3D illustrate an exemplary expandable pump portion that includes a blood conduit, a plurality of impellers, and a plurality of expandable scaffold sections or support members.
Figure 3C:
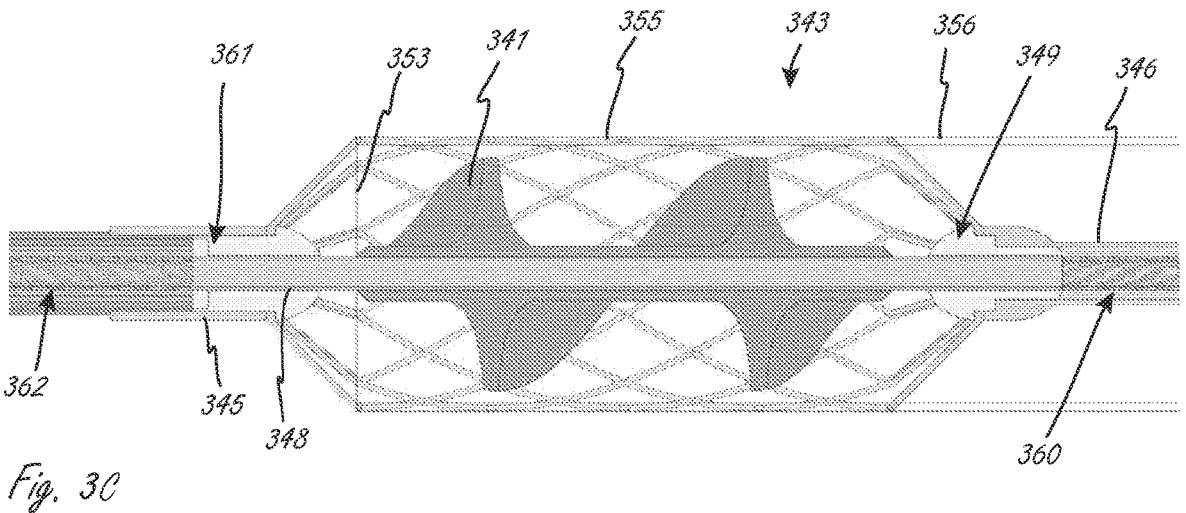
Figure 3D:
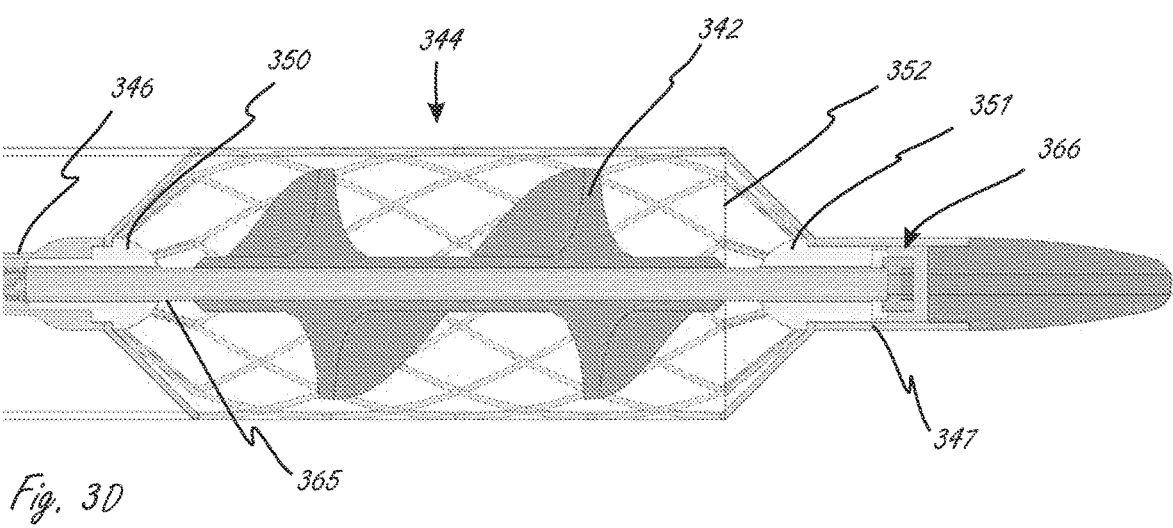

FIGS. 3A-3D show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
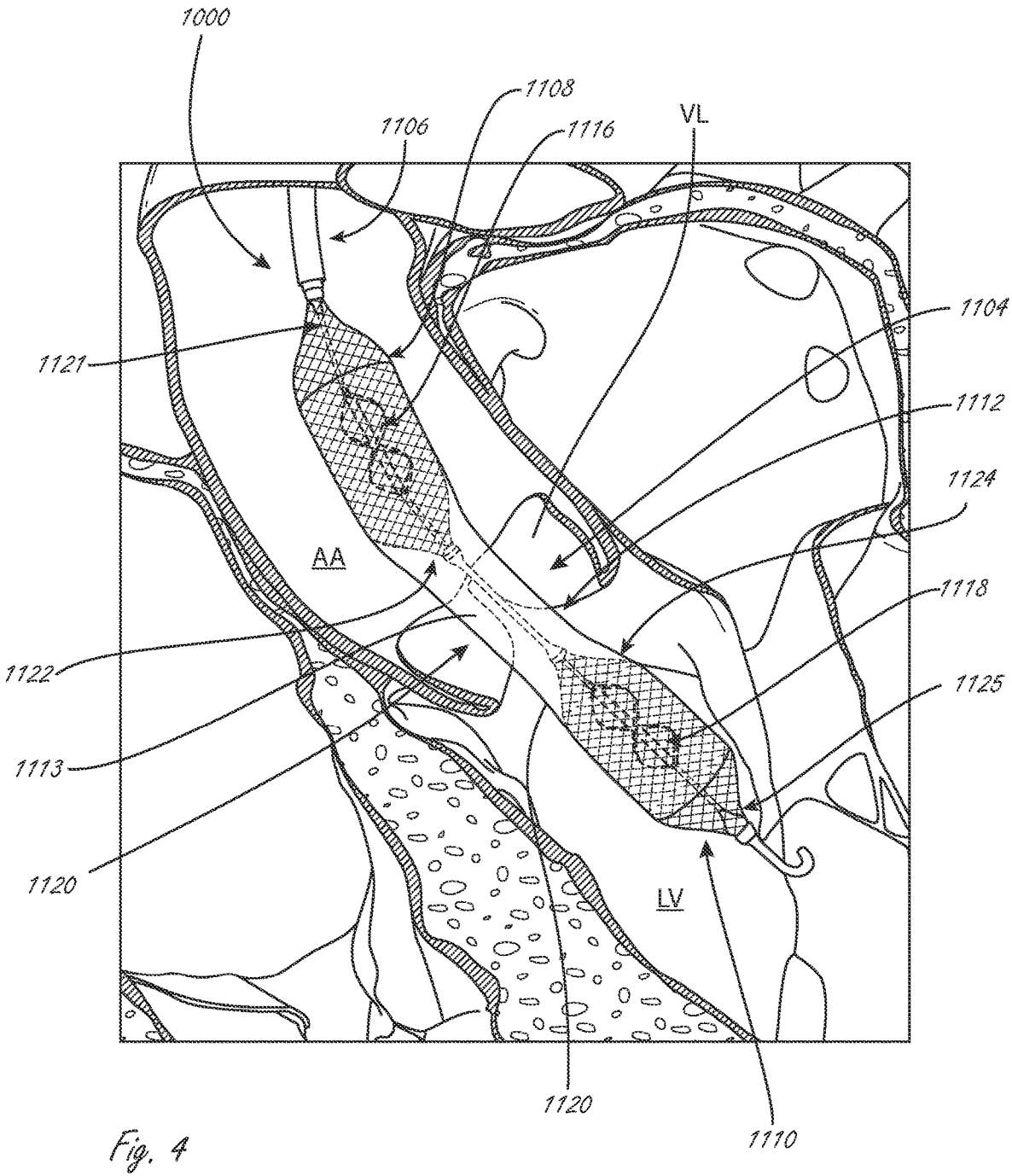
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. While the embodiment of FIG. 4 is shown with two impellers, it should be understood that other embodiments can include only a single impeller, such as a single proximal impeller. Once difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIGS. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. Nos. 6,533,716, or 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

In other embodiments, however, the working portion can include a single elongate expandable member. In this embodiment, as described above, a central region or section of the working portion can be more flexible than the proximal and distal regions or sections, to allow for more deformation of the central region at the location of the valve.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
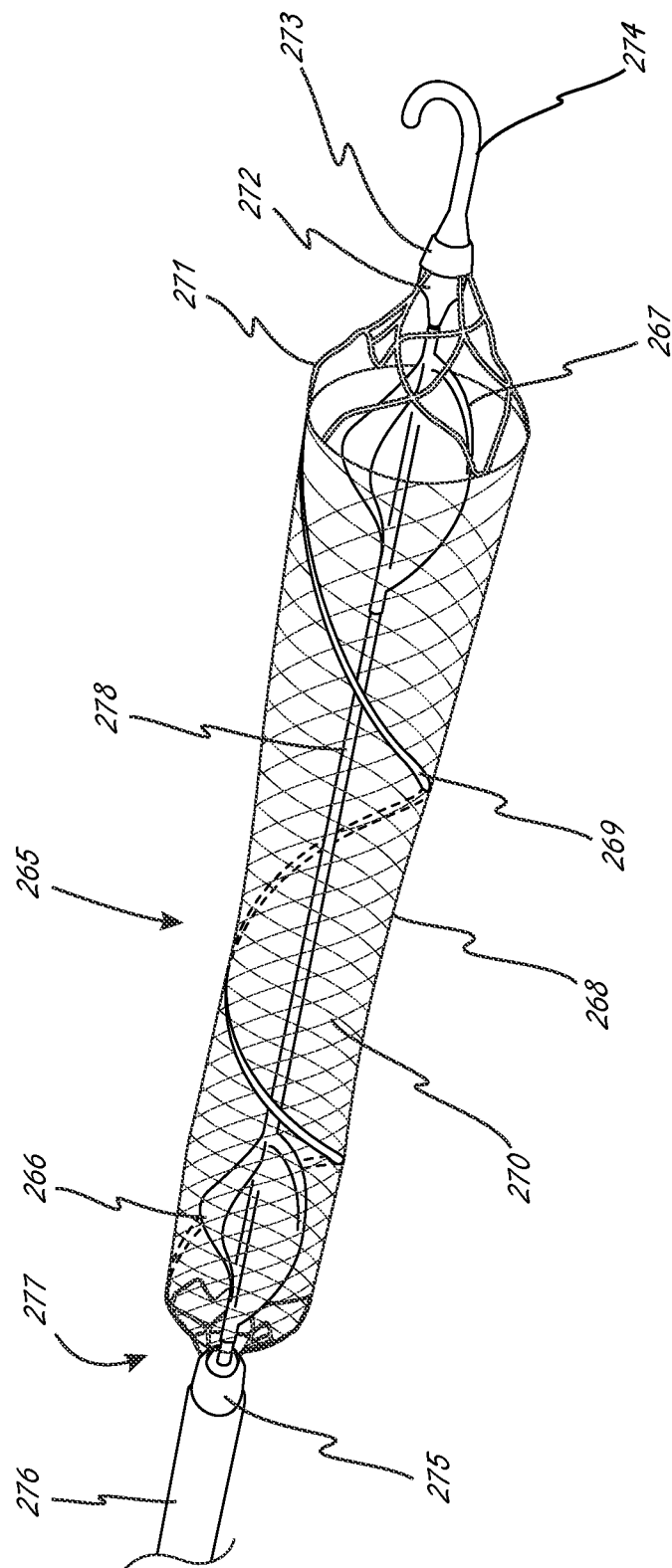
FIG. 5 illustrates an exemplary pump portion including an expandable impeller housing, a blood conduit, and a plurality of impellers.
Figure 5:
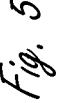

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. It should be understood that other embodiments of the working portion can include only a proximal impeller 266, and no distal impeller. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figures 6A, 6B, 6C, 7:
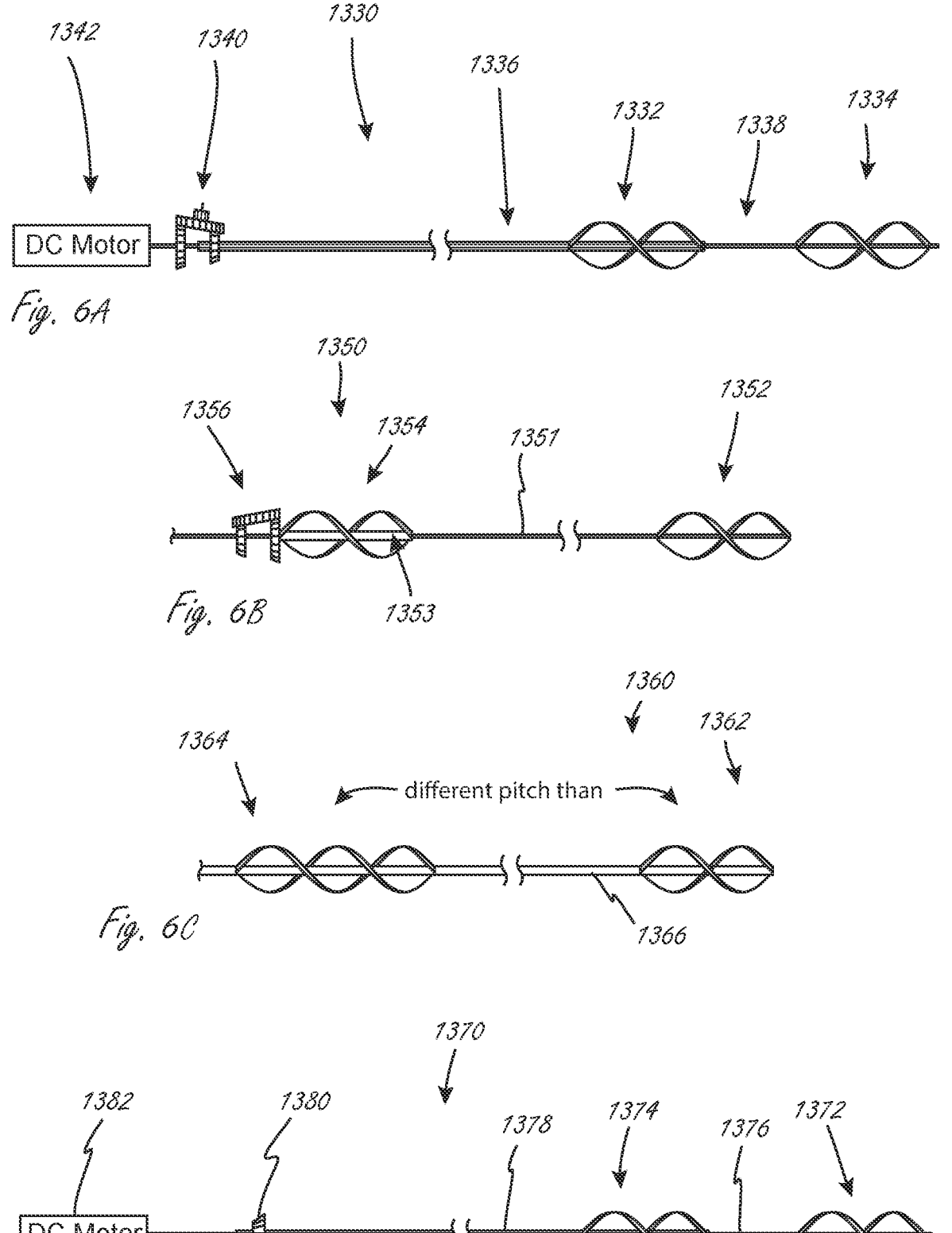
FIG. 6A illustrates at least a portion of an exemplary catheter blood pump that includes a pump portion, wherein at least two different impellers can be rotated at different speeds.
FIG. 6B illustrates at least a portion of an exemplary catheter blood pump that includes a pump portion, where at least two different impellers can be rotated at different speeds.
FIG. 6C illustrates at least a portion of an exemplary catheter blood pump that includes a pump portion with at least two impellers having different pitches.
FIG. 7 illustrates a portion of an exemplary catheter blood pump that includes a pump portion.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figures 8, 9:
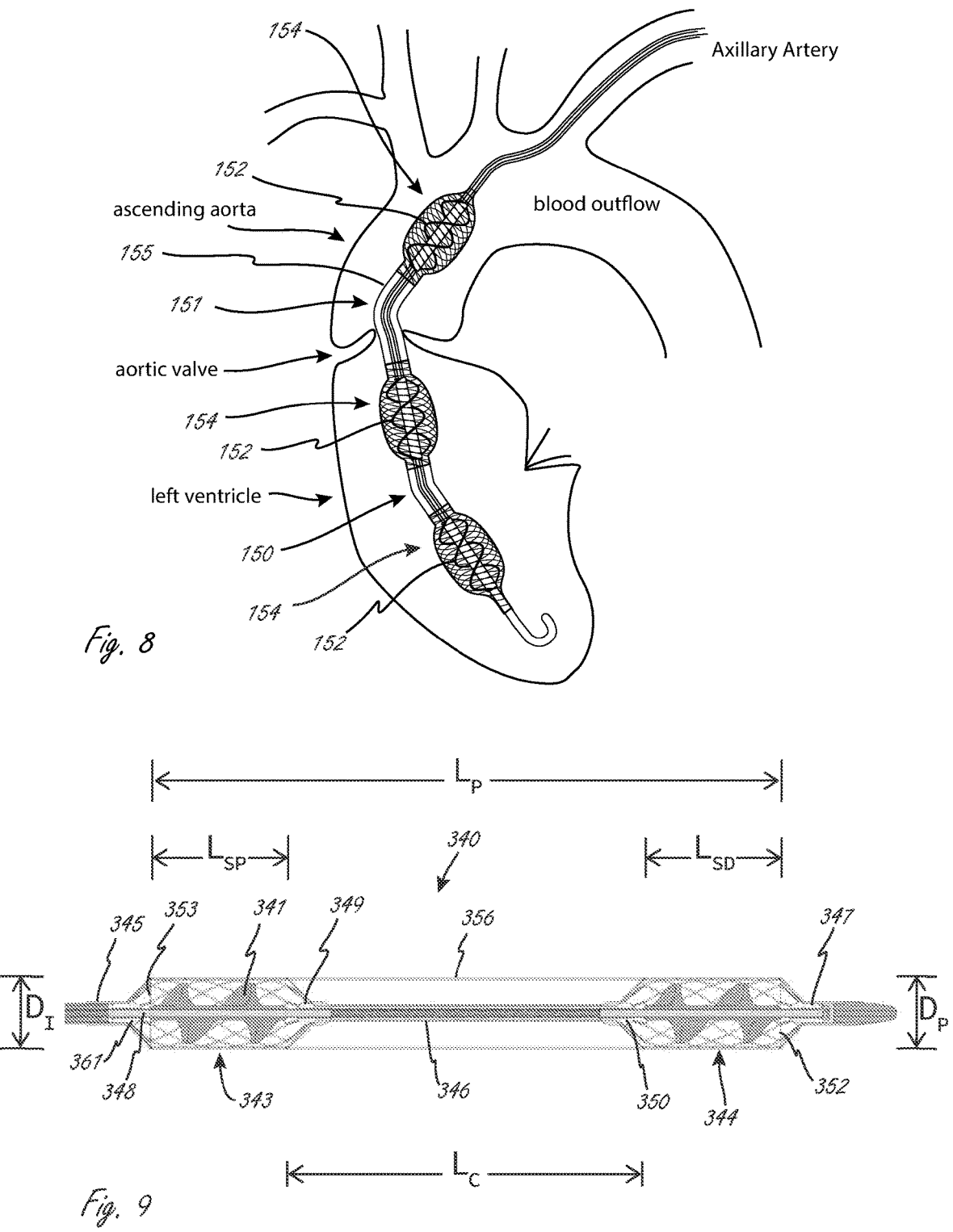
FIG. 8 illustrates an exemplary expandable pump portion including a plurality of expandable impellers, including one or more bends formed therein between adjacent impellers.
FIG. 9 illustrates an exemplary expandable pump portion comprising a plurality of impellers and a blood conduit.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

Figure 10:
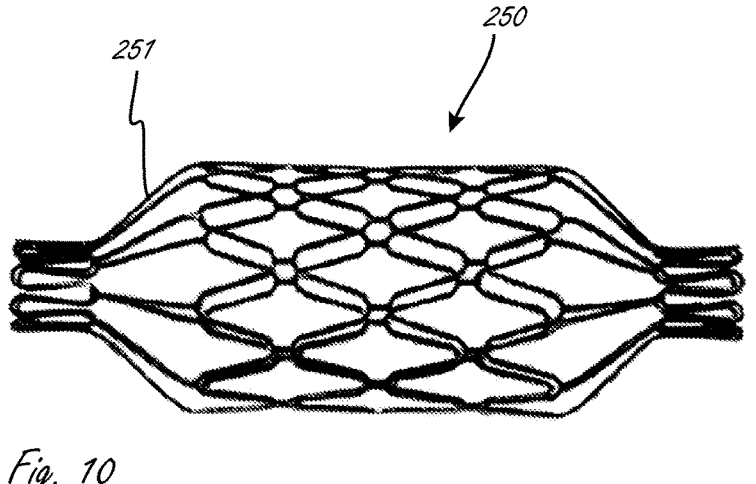
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
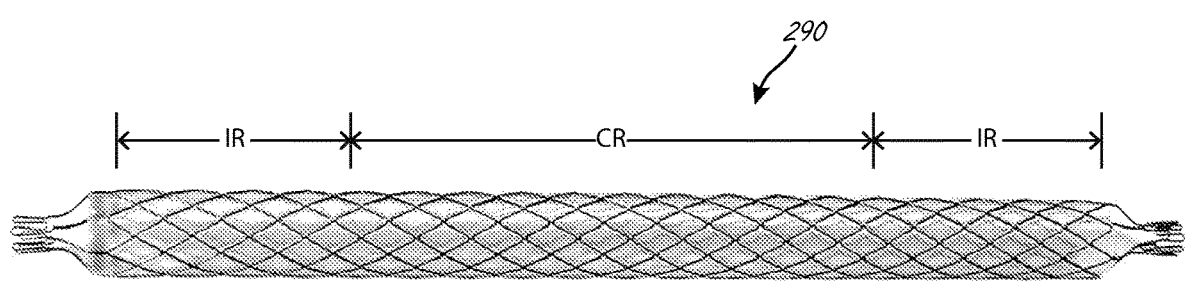
FIG. 11 illustrates an exemplary scaffold design and exemplary struts.

FIG. 11 show an exemplary scaffold along an length of the blood conduit. Central region "CR" may be axially between proximal and distal impellers. Central region "CR" flexibility is increased relative to scaffold impeller regions "IR" due to breaks or discontinuities in the scaffold pattern in the central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IR"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. It should be understood that in some embodiments, only a single impeller is implemented, such as a proximal impeller. Even with only a single impeller, it should be understood that both of the distal and proximal "IR" regions can have relatively less flexibility than the central region "CR" Exemplary benefits of the relative flexibility in these respective sections are described elsewhere herein. For example, if a proximal impeller is disposed in the proximal "IR" region and no distal impeller is disposed within the distal "IR" region, the distal "IR" region may still have more stiffness (or less flexibility) than the central region "CR". FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
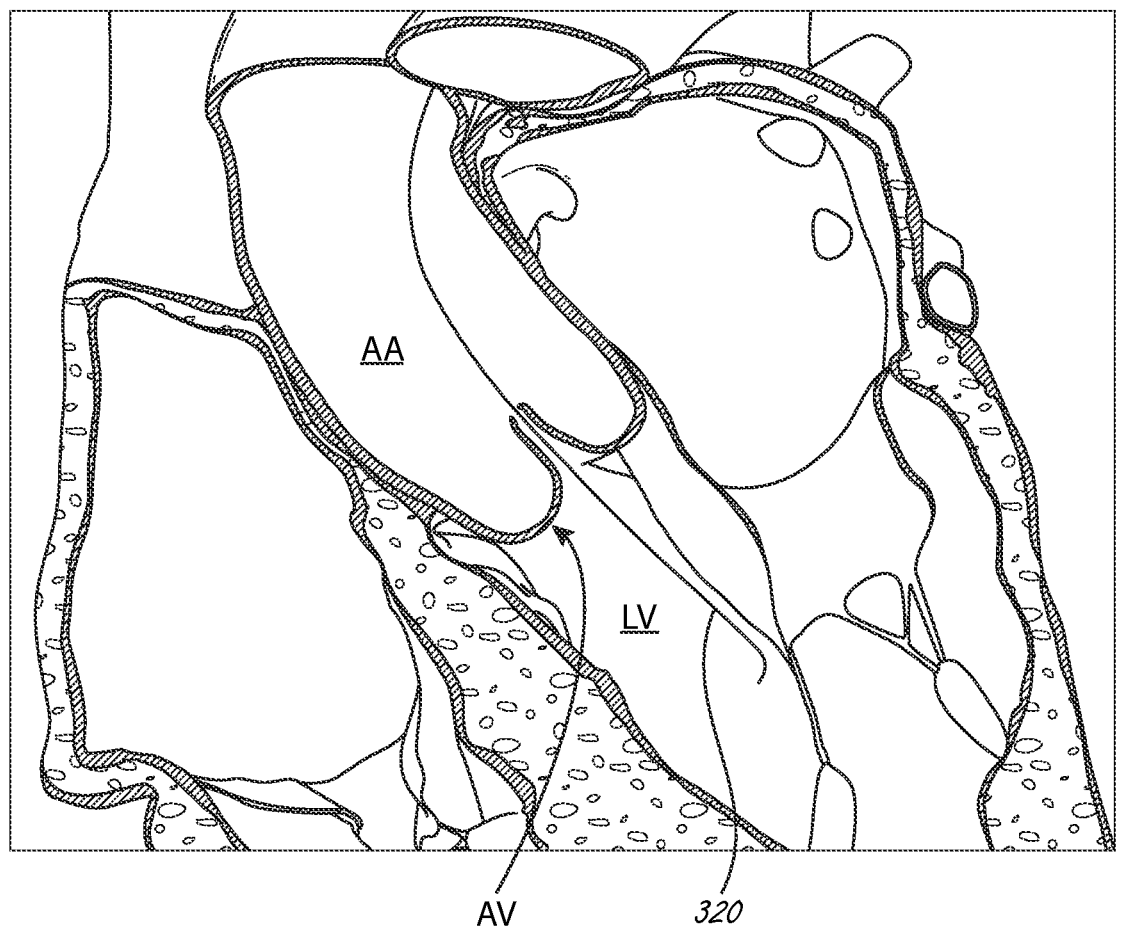
FIGS. 12A-12F illustrate an exemplary sequence of steps that may be performed to deploy an exemplary pump portion of a catheter blood pump.
Figure 12B:
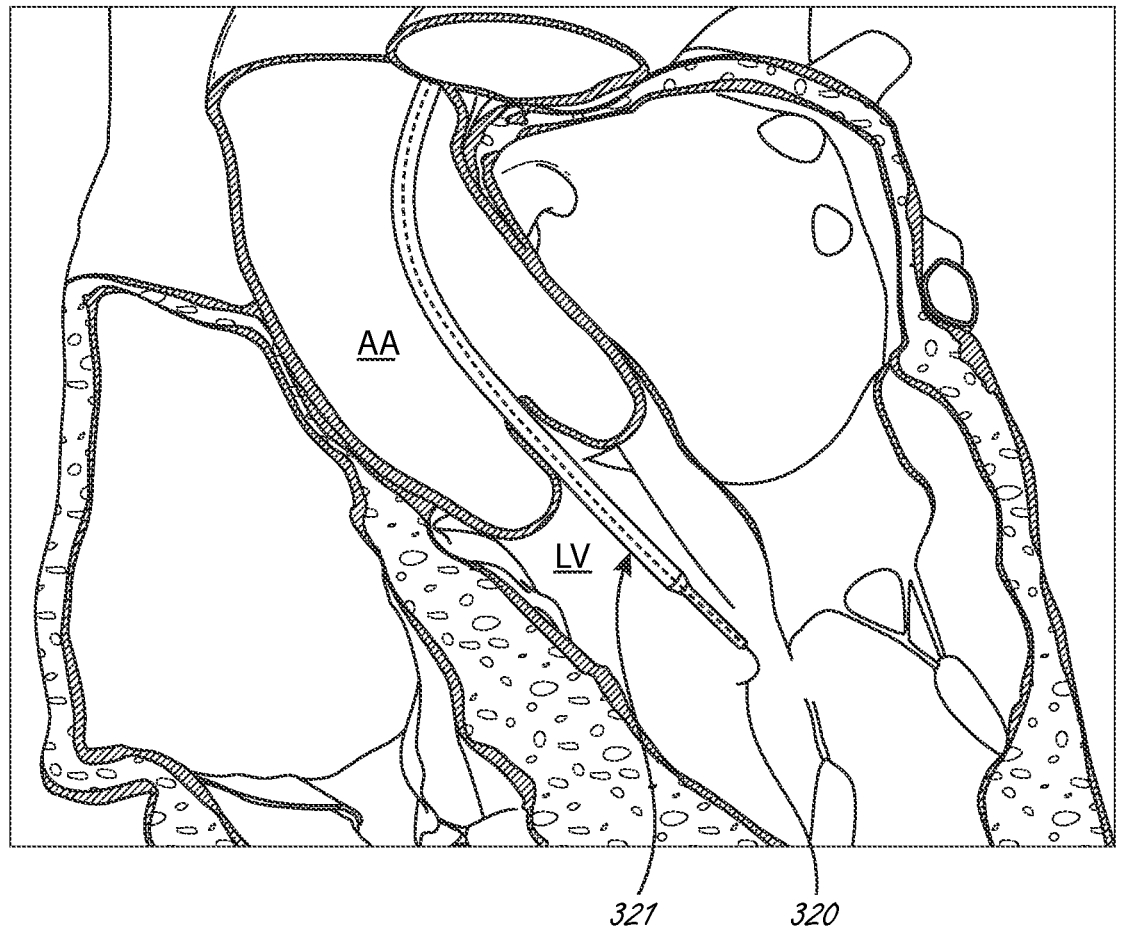

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning an aortic valve "AV," and into a target location (e.g., left ventricle "LV"), using, for example, one or more radiopaque markers to position the blood pump.

Figure 12C:
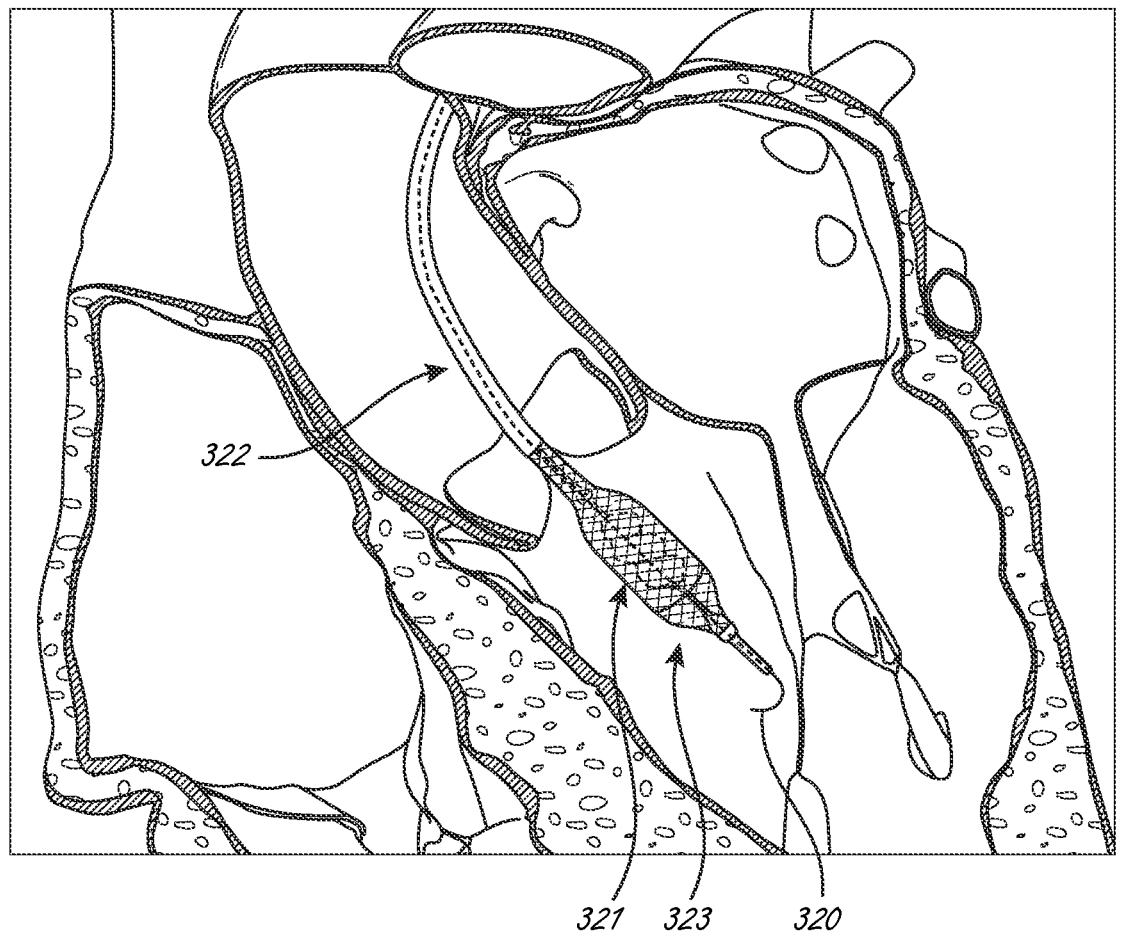
Figure 12D:
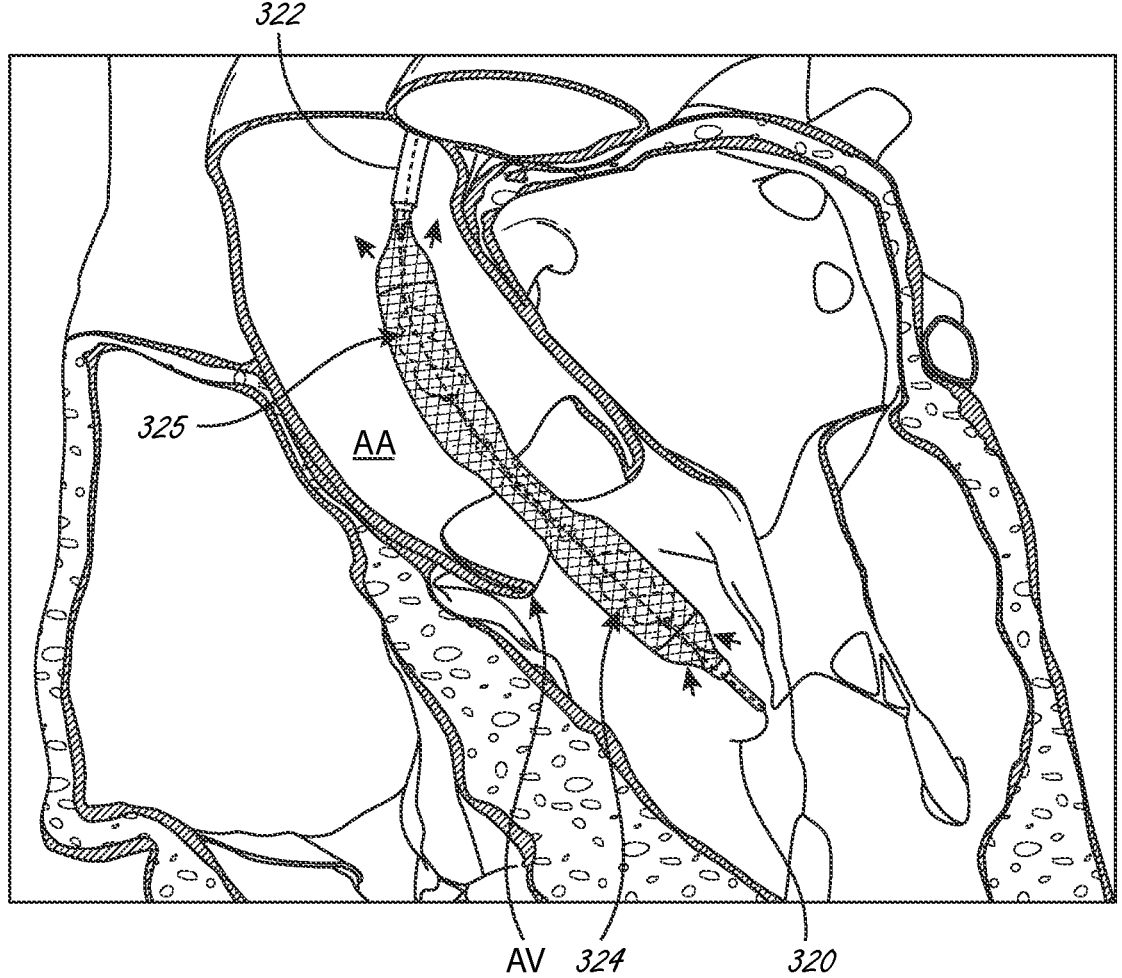

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 12E:
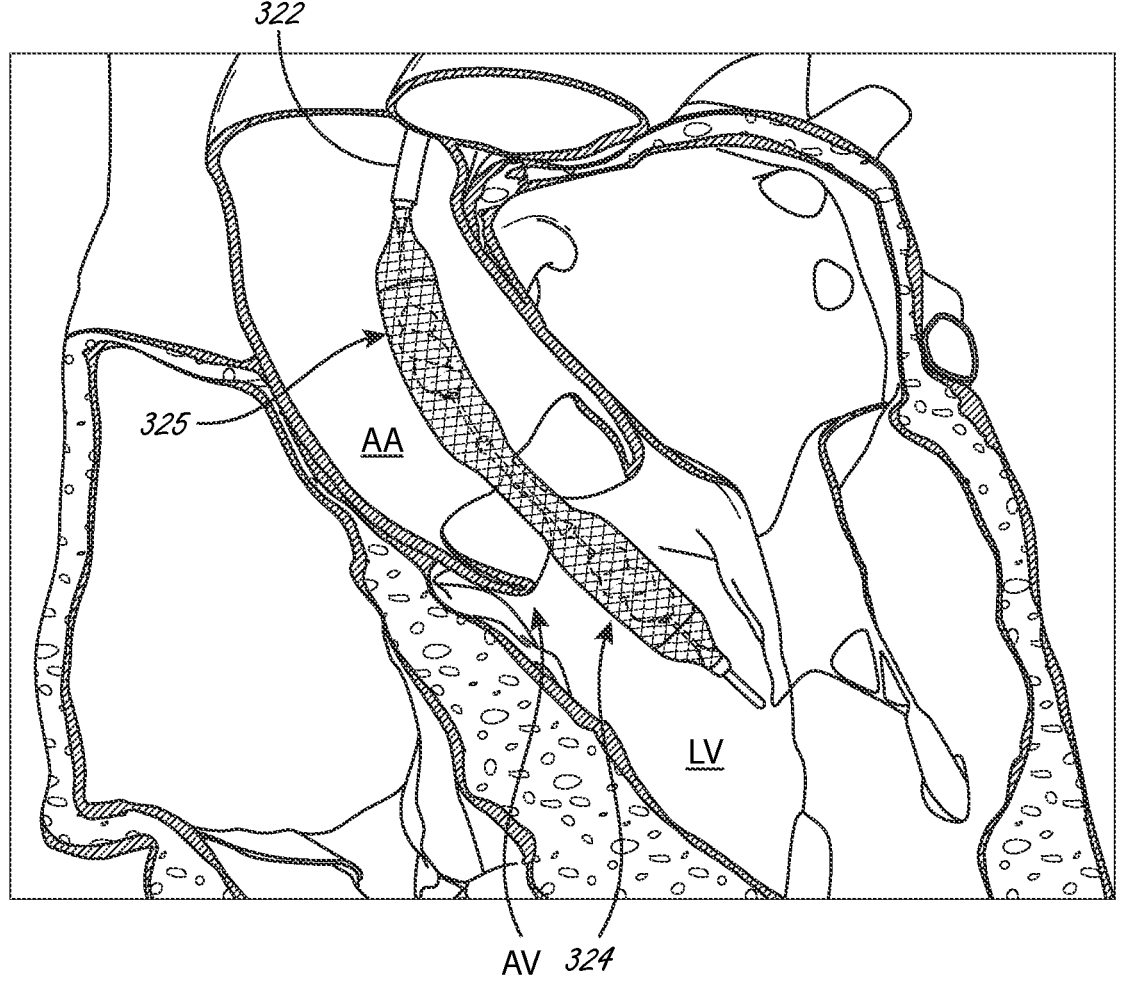
Figure 12F:
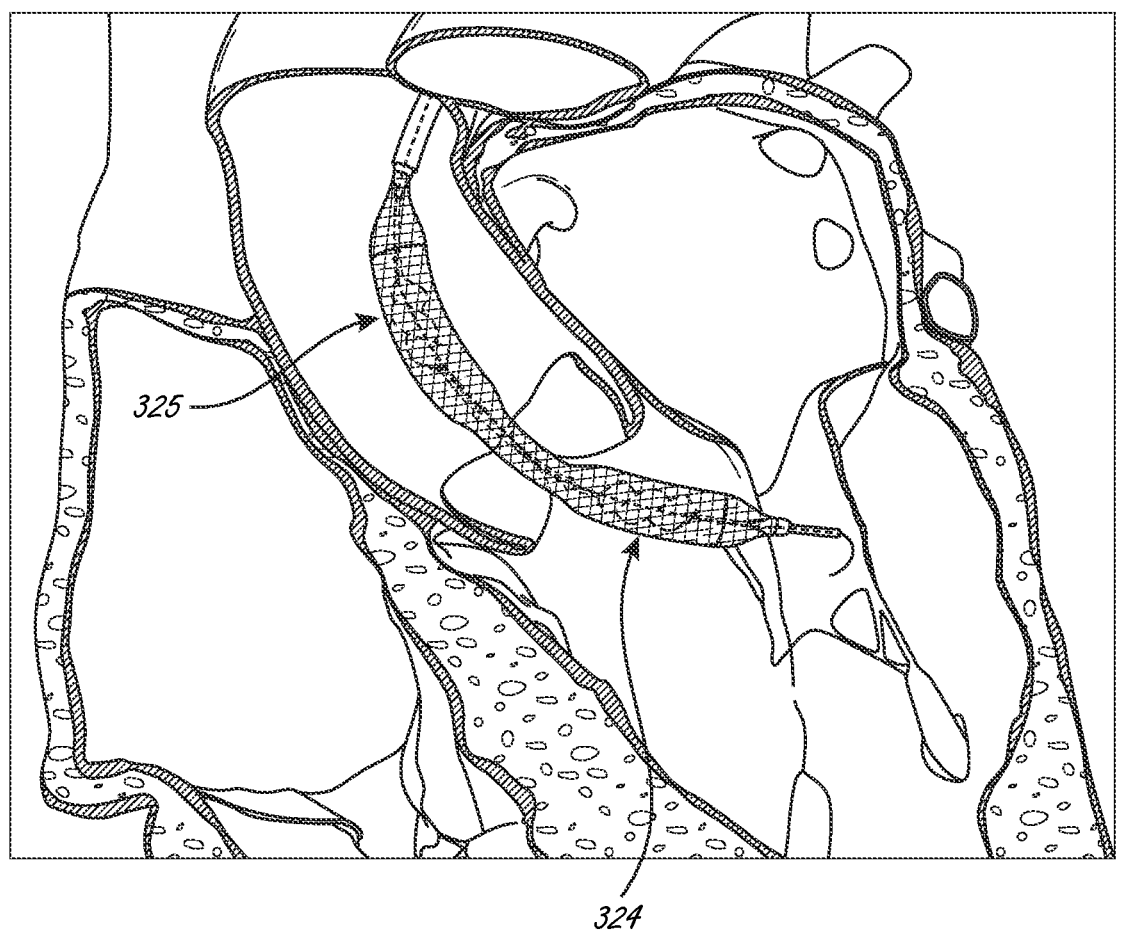

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figures.

As set forth above, this disclosure includes catheter blood pumps that include an expandable pump portion extending distally relative to a catheter. The pump portions include an impeller housing that includes an expandable blood conduit that defines a blood lumen. The blood conduit may include one or more scaffold sections that together may also be referred to herein as a single scaffold. In some exemplary embodiments the expandable blood conduit may include one or more of a proximal impeller scaffold, a distal impeller scaffold, and a central scaffold disposed between the proximal impeller scaffold and the distal impeller scaffold, where any combination thereof may also be referred to herein as a scaffold. Any individual proximal impeller scaffold or distal impeller scaffold may also be referred to herein as an expandable member, such as is shown in FIGS. 3A-3D. In some embodiments the expandable blood conduit may include a proximal impeller scaffold and additional scaffold extending distally therefrom, such as if the pump portion includes a proximal impeller but does not include a distal impeller. In any of the embodiments herein, a reference to a distal impeller is only by way of example, and pump portions herein need not include a distal impeller. Central scaffolds herein are generally less stiff in response to a radially inward force than a proximal scaffold, and optionally also less stiff than a distal scaffold, such as a distal impeller scaffold. Exemplary advantages of central scaffold sections that are less stiffness are set forth elsewhere herein. The blood conduit may also include a membrane coupled to the one or more scaffolds, the membrane at least partially defining the blood lumen. Membranes in this context may incorporate by reference herein the disclosure of conduits, including any feature or method of manufacturing described above. The catheter blood pumps may include an impeller disposed in a proximal region of the impeller housing, which may be a proximal impeller. The catheter blood pumps may also include a distal impeller in a distal region of the impeller housing. Exemplary impellers, including exemplary proximal and distal impellers, are set forth herein by way of example. An impeller that is at least partially within a portion of a scaffold may be described with respect to the relative position of the scaffold, such the a proximal impeller within at least a portion of a proximal scaffold, or a distal impeller within at least a portion of a distal scaffold.

When a proximal impeller is described as being within a proximal scaffold, it is understood that the proximal scaffold need not axially extend over an entire length of the impeller, as long as there is some amount of axial overlap. For example, some proximal impellers herein extend proximally from a blood conduit, and a proximal region of the proximal impeller is not surrounded by a blood conduit scaffold, while a distal region of the impeller is surrounded by scaffold. Similarly, when a distal impeller herein (if the pump includes a distal impeller) is described as being within a distal scaffold, it is understood that the distal scaffold need not axially extend over an entire length of the impeller, as long as there is some degree of axial overlap therebetween.

Figures 13A, 13B, 13C:
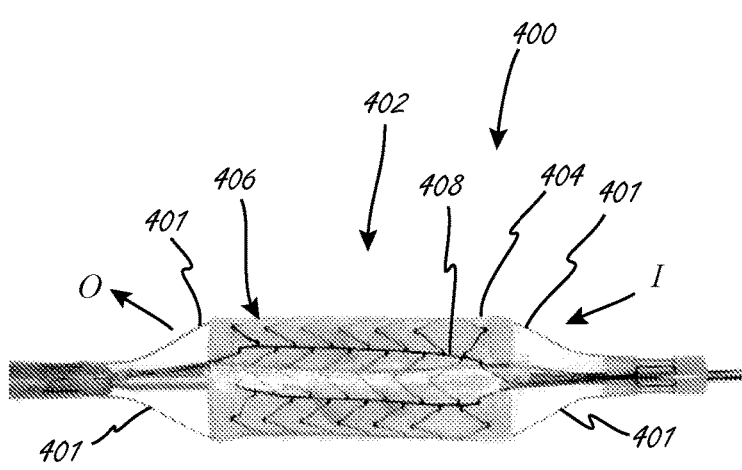
FIGS. 13A and 13B illustrate exemplary portions of an expandable pump portion.
FIG. 13C illustrates a scaffold from FIGS. 13A and 13B shown in a flattened and non-expanded configuration, as well as optional distal and proximal struts extending axially therefrom.

FIGS. 13A-13C illustrate exemplary designs for expandable scaffolds herein, which may at least partially surround an impeller that is at least partially disposed within a conduit that creates a fluid lumen. The scaffold patterns in FIGS. 13A-13C may be scaffold patterns that only extend over a particular impeller (e.g., a proximal basket or distal basket), or they may be scaffold patterns that extend over an entire blood conduit scaffold. Additional scaffold patterns that can be used with any embodiment of a blood pump or blood conduit are described and illustrated in PCT Application PCT/US2022/019187, filed Mar. 7, 2022, which is incorporated herein by reference in its entirety.

FIGS. 13A-13C illustrate expandable support members or scaffolds that each have an expanded configuration, wherein in the expanded configuration the support member has a plurality of continuous axially extending elements (e.g., 408, 410, 420, 430, 440) that are continuous and axially extending over at least 50% of a length of the expandable support member (e.g., $L_s$), and wherein the expandable support member includes a plurality of sets of connectors (e.g., 412/414, 409, 422/424, 432/434, 442/444) each set of connectors extending between first and second circumferentially adjacent continuous axially extending elements. In some embodiment the axially extending elements are linear or substantially linear.

FIGS. 13A-13C illustrate an exemplary pump portion 400 or a portion thereof that comprises an expandable impeller housing 402, wherein the expandable impeller housing having a blood conduit 404, the conduit defining a blood lumen between an housing inflow "I" and a housing outflow "O". The expandable impeller housing also includes an expandable scaffold or support member 406 at least partially surrounding an impeller (not shown in FIGS. 13A-13C) that is at least partially disposed within the conduit.

FIGS. 13A-13C illustrate an expandable impeller housing that includes a plurality of axially extending elements 408 circumferentially spaced apart around the housing 402 from adjacent axially extending elements, as shown. FIGS. 13A and 13B show an expanded configuration of the housing, while FIG. 13C illustrates a model of a flat, unexpanded configuration with unitary struts 401 extending axially therefrom, as shown. The plurality of axially extending elements may be referred to as "elements" in the context of scaffolds for simplicity, but it is understood that they are not to be considered any other type of "element" herein unless specifically indicated as such. The elements in this embodiment may be axial and linear in the housing expanded configuration. Expandable scaffold 406 also includes circumferential connectors 409 that circumferentially connect adjacent axial elements and extend from one axial element to an adjacent axial element. In this exemplary embodiment all of the connectors have the same general configuration, which includes first and second segments meeting at a rounded peak that is oriented axially (proximally or distally depending on the reference frame), otherwise stated as pointing axially. Length Ls of the scaffold and length Le of the elements is illustrated in FIG. 13C. Optional struts 401 are shown (which may be unitary with the scaffold). The axial elements 408 in this embodiment extend from a first axial element end 405 to second axial element end 405', which extend almost the entire length of the scaffold Ls. As shown, ends 405' of the elements (only one labeled) extend to a distal end region 407' of the scaffold 406. End 405 extends to proximal end region 407. The pump portion also includes a transition region 411, which includes circumferential extensions of adjacent axial elements, after which they meet to form a strut 401, as shown.

The scaffolds and blood conduit embodiments in FIGS. 13A-13C are illustrative, and may be modified to include aspects of other embodiments herein. The following description may provide modifications to the scaffolds in FIGS. 13A-13C, any of which may be incorporated into any of the scaffolds in FIGS. 13A-13C.

In any of the scaffolds shown in FIGS. 13A-13C, at least a first end of each of the plurality of axially extending elements may extend to one or more of a proximal end region (e.g., 417', 407') and a distal end region (e.g., 417,) of the expandable scaffold.

In any of the scaffolds shown in FIGS. 13A-13C, at least one of, and optionally all of, the plurality of axially extending elements may be linear. In any of the scaffolds shown in FIGS. 13A-13C, at least one of, and optionally all of, the plurality of axially extending elements may be curvilinear.

In any of the scaffolds shown in FIGS. 13A-13C, each one of the the plurality of axially extending elements may have proximal and distal ends, wherein the proximal and distal ends are substantially circumferentially aligned.

In any of the scaffolds shown in FIGS. 13A-13C, each of the the plurality of axially extending elements may have a circumferential span that is not larger than 10 degrees circumferentially around the expandable scaffold, optionally not larger than 5 degrees of the expandable scaffold.

In any of the scaffolds shown in FIGS. 13A-13C, each of the the plurality of axially extending elements may follow a path that is substantially parallel with a longitudinal axis of the expandable scaffold.

In any of the embodiments in FIGS. 13A-13C, each of the the plurality of axially extending elements may be continuous and axially extending over at least 55% of a length of the expandable scaffold, optionally over at least 60%, optionally over at least 65%, optionally over at least 70%, optionally over at least 75%, optionally over at least 80%, optionally over at least 85%, optionally over at least 90, optionally over at least 95.

In any of the scaffolds shown in FIGS. 13A-13C, all of the connectors in all of the sets of the plurality of sets of connectors may have the same configuration. In any of the scaffolds shown in FIGS. 13A-13C, all of the connectors in all of the sets of the plurality of sets of connectors may not have the same configuration. In any of the scaffolds shown in FIGS. 13A-13C, each individual set of connectors may have a plurality of connectors that have the same configuration. In any of the embodiments in FIGS. 13A-13C, all of the connectors in all of the sets of the plurality of sets of connectors may have an S-shape. In any of the embodiments in FIGS. 13A-13C all of the connectors in all of the sets of the plurality of sets of connectors may have a reverse (or inverted) S-shape. In any of the scaffolds shown in FIGS.

13A-13C, all of the connectors in a first set of connectors may have a S shape. In any of the scaffolds shown in FIGS. 13A-13C, a second set of connectors that is circumferentially adjacent to the first set of connectors may all have an inverted S shape. In any of the scaffolds shown in FIGS. 13A-13C, S shape/inverted S shape connectors may alternate around the circumference of the expandable scaffold.

In any of the embodiments in FIGS. 13A-13C, a first set of connectors that extend in a first circumferential direction from a first axially extending element may extend from the first axially extending element at axial locations that are different from the axial locations at which a second set of connectors extend from the first axially extending element in a second circumferential direction (i.e., the connectors have ends that are axially offset).

In any of the embodiments in FIGS. 13A-13C, the expandable scaffold may include a transition region connecting a first axially extending element with a strut, optionally wherein the transition region is considered part of the expandable scaffold. A transition region may also connect the strut with a second axially extending element, the second axially being circumferentially adjacent to the first axially extending around the blood conduit. In any of the scaffolds shown in FIGS. 13A-13C, the expandable scaffold may extend along substantially the entire length of the conduit. In any of the scaffolds shown in FIGS. 13A-13C, the expandable scaffold may extend along less than 50% of the length of the expandable impeller housing. In any of the embodiments in FIGS. 13A-13C, the expandable scaffold may extend only in a region of the expandable housing in which an impeller is disposed.

In any of the embodiments in FIGS. 13A-13C, the expandable impeller housing may include a second expandable scaffold axially spaced from the first expandable scaffold. A second expandable scaffold may have an expanded configuration with a second plurality of axially extending elements that are axially extending over at least 50% of a length of the second expandable scaffold and wherein the second expandable scaffold may also include a plurality of sets of connectors, each set of connectors extending circumferentially between first and second circumferentially adjacent axially extending elements. A second expandable scaffold may include any features set forth in any of the claims or described elsewhere herein. In any of the scaffolds shown in FIGS. 13A-13C, the expandable scaffold may be unitary, that is, made from a single piece of starting material.

In any of the embodiments herein, a distal scaffold may have a length that is greater than a length of a proximal scaffold. In any of the embodiments herein, a distal scaffold may have a length that is less than a length of a proximal scaffold. In any of the embodiments herein, a distal scaffold may have a length that is the same as a length of a proximal scaffold.

In any embodiment herein, a central scaffold may have a length that is greater than a length of one or both of a proximal scaffold and a distal scaffold.

Any of the different scaffold sections herein may be connected with one or more welds, and may not be unitary with each other.

In any of the embodiments herein, any section or sections of the scaffold may have a thickness (measured radially between a scaffold inner diameter and a scaffold outer diameter) that is the same as or different than a thickness of any other section of the scaffold. For example, a thickness of a scaffold section may be decreased by electropolishing one or more sections more than other sections (which may include no electropolishing). Varying the thickness may be in addition to or alternative to varying the width, which may allow for more design options, as may be desired.

In any of the embodiments herein, an axial distance between proximal and distal scaffold sections may be from 30 mm to 50 mm, such as from 35 mm to 45 mm.

In any of the embodiments herein, the pump portion may be from 40 mm and 80 mm, such as from 50 mm to 70 mm, such as from 55 mm to 65 cm.

In any of the embodiments herein that include first and second impellers, an axial distance between impellers may be from 40 mm to 60 mm, such as from 45 mm to 55 mm.

In any of the embodiments herein, a diameter of the expanded (or non-collapsed) blood conduit may be from 6 mm to 8.5 mm, such as from 6 mm to 8 mm, such as from 6.5 mm to 7.5 mm In any of the embodiments herein, a diameter of any of the impellers when expanded may be from 5 mm to 7 mm, such as from 5.5 mm to 6.5 mm.

The disclosure herein and below includes catheter blood pumps that include a pump portion and an elongate body coupled thereto, wherein the elongate body is generally non expandable and extends proximally from the pump portion, optionally towards a motor that may be disposed outside of the patient when the pump portion is in use. In some applications, depending on the anatomical placement of the pump portion and/or the access pathway to position the pump portion in the desired location, it may be beneficial for at least a portion of the catheter blood pump to have sufficiently flexibility such that it can accommodate the shape of the anatomy in which it is placed, while also ensuring the pump portion is placed in its target location and functions properly. In some uses, the pump portion may be positioned across an aortic valve, with the elongate body extending proximally from the pump and through the aortic arch. The placement in this location causes at least a portion of the elongate body to assume a bend through the ascending aorta and along the arch while the pump portion is across the valve. It may be beneficial for the catheter blood pump to include a region proximal to and as close as possible to the pump portion that is configured to be relatively easily bent or deflected so that the region preferentially absorbs forces and minimizes the amount of forces and/or bending that is translated further distally to the pump portion. Incorporating a preferential bending region that is proximal to and near to the pump portion that is adapted to preferentially absorb forces and prevent the pump from bending may reduce the likelihood of a pump impeller axis and blood conduit axis becoming misaligned and preventing proper pump performance Additionally or alternatively, a preferential bending region in a distal region of the elongate body proximal to the pump portion may be adapted and configured to bend more easily than adjacent regions, which may facilitate relatively greater bending in the preferential bending region and help position and orient the pump portion across the valve in a desired position. Additionally, the motion of the heart beats will generally apply force to at least some portion of the distal region (e.g., at least some portion of the pump portion and/or a distal region of the elongate body) of the catheter blood pump. Catheter blood pumps that incorporate a preferential bending zone in a region proximal to the pump portion can preferentially absorb the repeating force due to the pumping heart in a particular distal region of the elongate body and minimize those forces from translating distally towards the pump portion. There may be additional advantages of including a distal end region of the elongate body that includes a preferential bending zone or is more flexible than adjacent regions of the catheter blood pump.

FIGS. 14A-14E illustrate merely exemplary embodiments of catheter blood pumps that include an elongate body extending proximally from a pump portion, wherein a distal region of the elongate body includes a preferential bending zone or region that is configured to more easily bend than regions of the catheter blood pump that are proximally and distally adjacent to the preferential bending region. The flexibility of the preferential bending zone may optionally vary along its length, although in some embodiments the flexibility may be constant or substantially constant along its length.

Figure 14A:
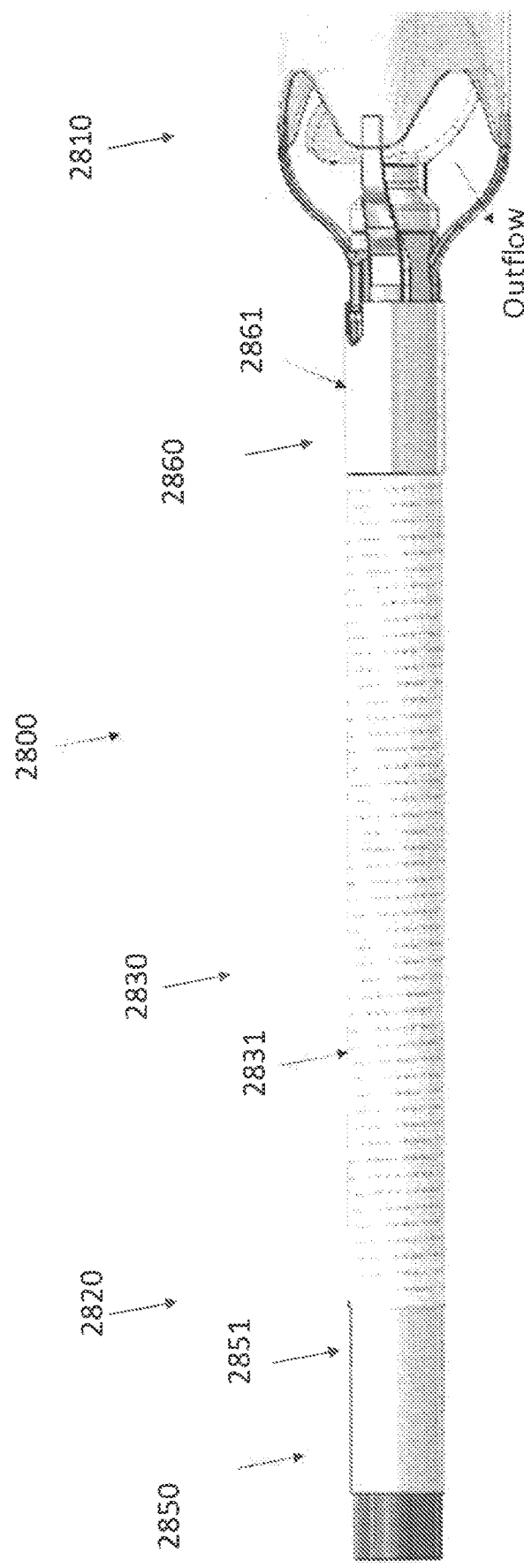
FIGS. 14A-14F illustrate merely exemplary embodiments of catheter blood pumps that include an elongate body extending proximally from a pump portion, wherein a distal region of the elongate body includes a preferential bending zone or region that is configured to more easily bend that regions of the catheter blood pump that are proximally and distally adjacent to the preferential bending region.

FIG. 14A illustrates a side view of a portion of an exemplary catheter blood pump 2800, which includes pump portion 2810 and elongate body 2820 shown coupled to the pump portion 2810 and extending proximally relative thereto. Elongate body 2820 includes preferential bending zone or region 2830, which as shown is in a distal region of elongate body 2820 and near or adjacent to the pump portion 2810. Pump portion 2810 may be any of the pump portions herein, or may comprise one or more aspects of any of the pump portions herein. Preferential bending zones or regions herein may also be referred to as flexible regions, or relatively more flexible regions compared to adjacent regions of the elongate body. In this example, preferential bending zone 2830 is more flexible than proximal adjacent region 2850 and distal adjacent region 2860, which are axially adjacent to bending region 2830 on either side thereof. In another embodiment, the preferential pending zone 2830 extends all the way to the outflow regions of the pump portion 2810, and there is no distal region 2860 distal to the preferential bending region.

In this example, distal region 2860 may comprise a bearing housing region, and may include therein one or or more bearings associated with the rotation of a rotational drive assembly that extends through preferential bending zone 2830, distal region 2860 and through one or more impellers in pump portion 2810. Distal region 2860 may also generally be considered a coupling region to which the pump portion 2810 is coupled. One or more of bearing components or coupling components in distal region 2860 may contribute to distal region 2860 being stiffer than preferential bending zone 2830. There is generally a difference in stiffness between the most flexible region of preferential bending zone 2830 and distal region 2860. To avoid kinking between the preferential bending zone and distal region 2860, the distal region of preferential bending zone 2830 may include a transition region that has a stiffness in between the stiffness of the most flexible portion of preferential bending zone 2830 and distal region 2860. Exemplary transition zones are described below with respect to exemplary laser cut patterns.

Additionally (in this example), proximal region 2850 is stiffer or less flexible than preferential bending region 2830. Proximal region 2850 may include one or more coupling components that are configured to couple a proximal catheter shaft region to a preferential bending zone, wherein optionally one or more coupling components in proximal region 2850 contribute to the proximal region 2850 being stiffer or less flexible than preferential bending zone 2830. In some alternative examples, one or more of a catheter shaft (e.g., 2840) or a retractable sheath (e.g., 2890) may contribute to first region 2850 being stiffer or less flexible than preferential bending zone 2830. In some examples one or both of a catheter shaft or a sheath may comprise a polymeric material. It is generally desirable to avoid kinking between the relatively stiff proximal region 2850 and preferential bending zone 2830, and thus the proximal region of preferential bending zone 2830 may include a transition region in which the flexibility is in between that of the most flexible portion of the preferential bending zone and the flexibility of proximal region 2850. The proximal and distal regions of the preferential bending zone may thus include flexibility transition zones to avoid kinking between the the preferential bending zone and the relatively stiffer proximal region 2850 and the relatively stiffer distal region 2860. The transition zones may have discrete sections of different flexibility and/or they may include sections with continuously varying flexibility. Exemplary transition zones and exemplary methods of imparting varying flexibility into the preferential bending zone are described below with reference to laser cut patterns.

Figure 14B:
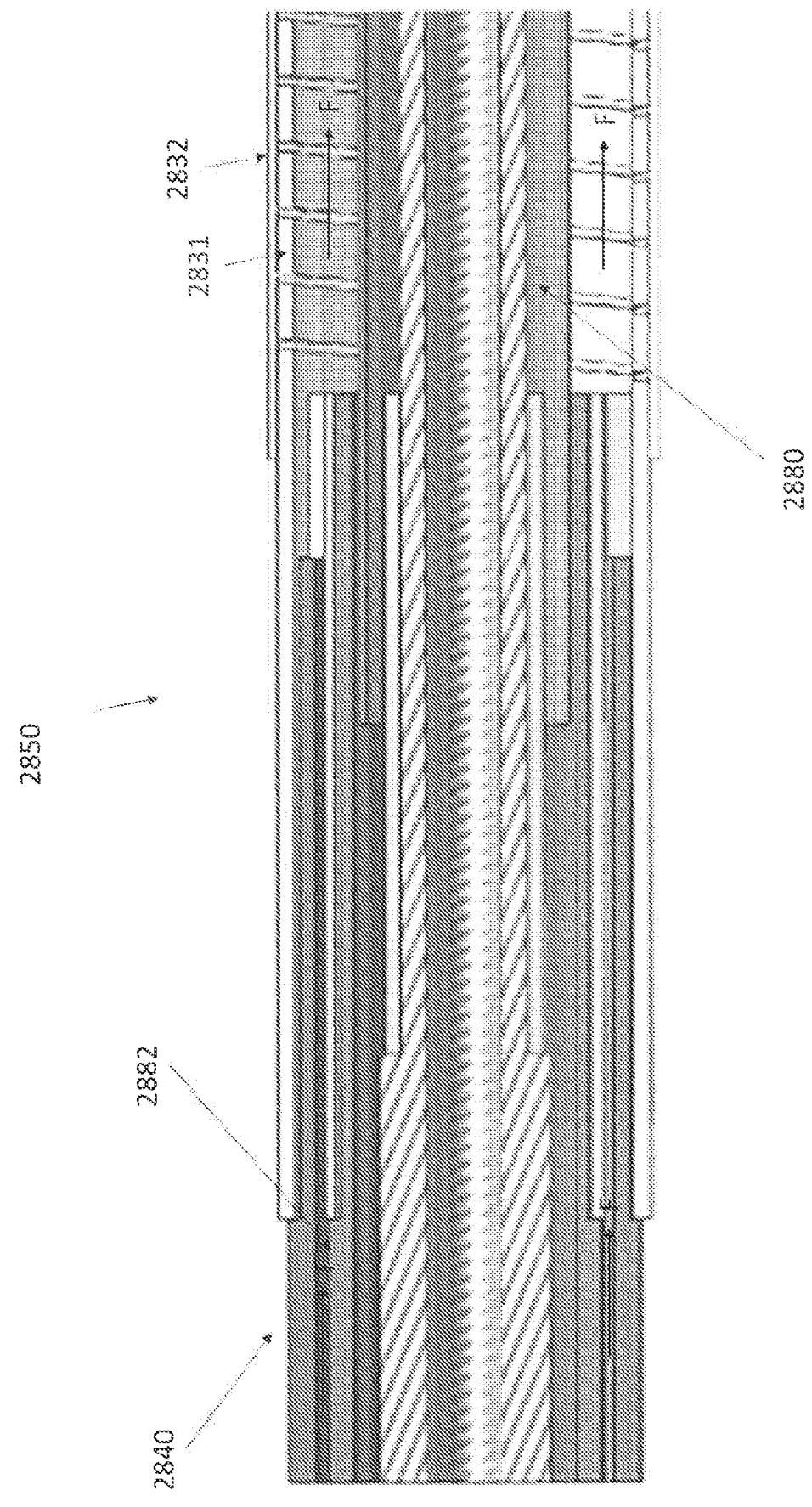
Figure 14C:
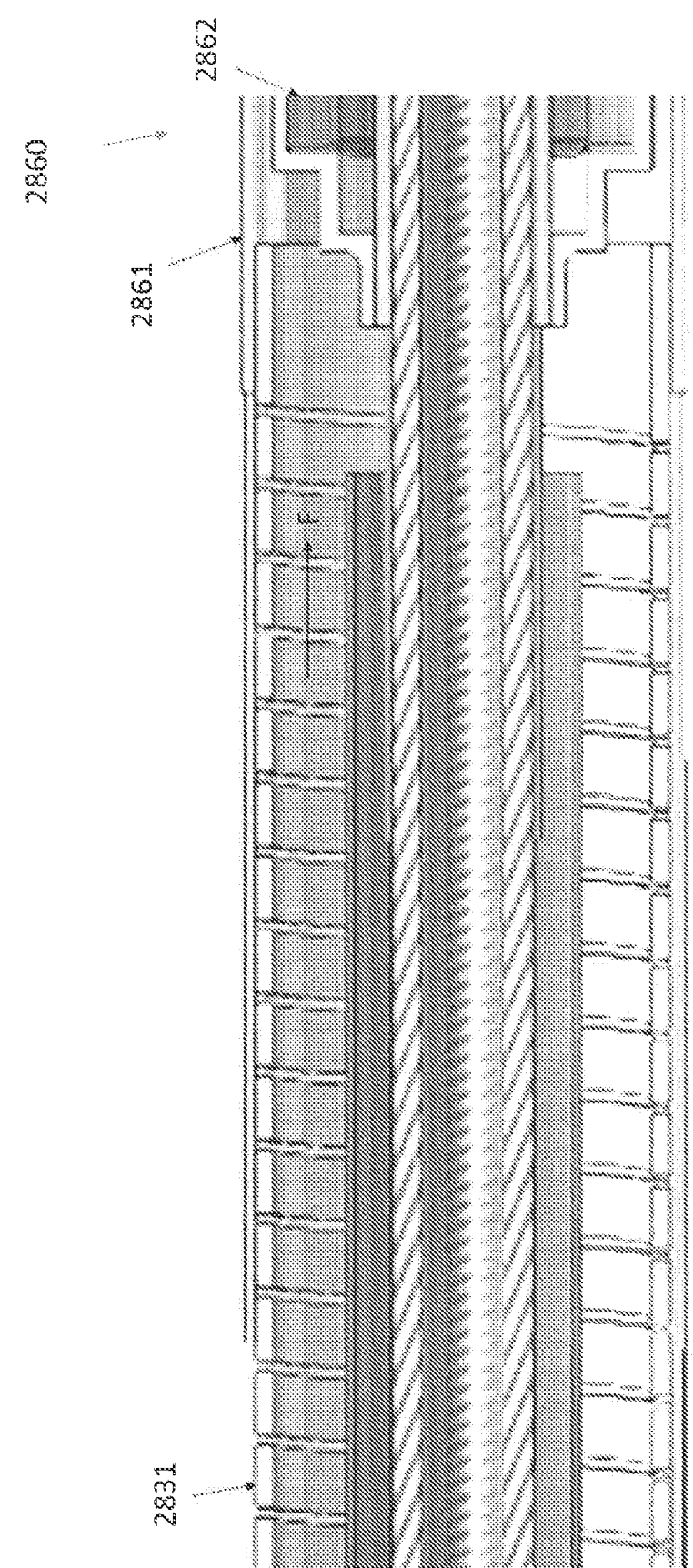
Figure 14D:
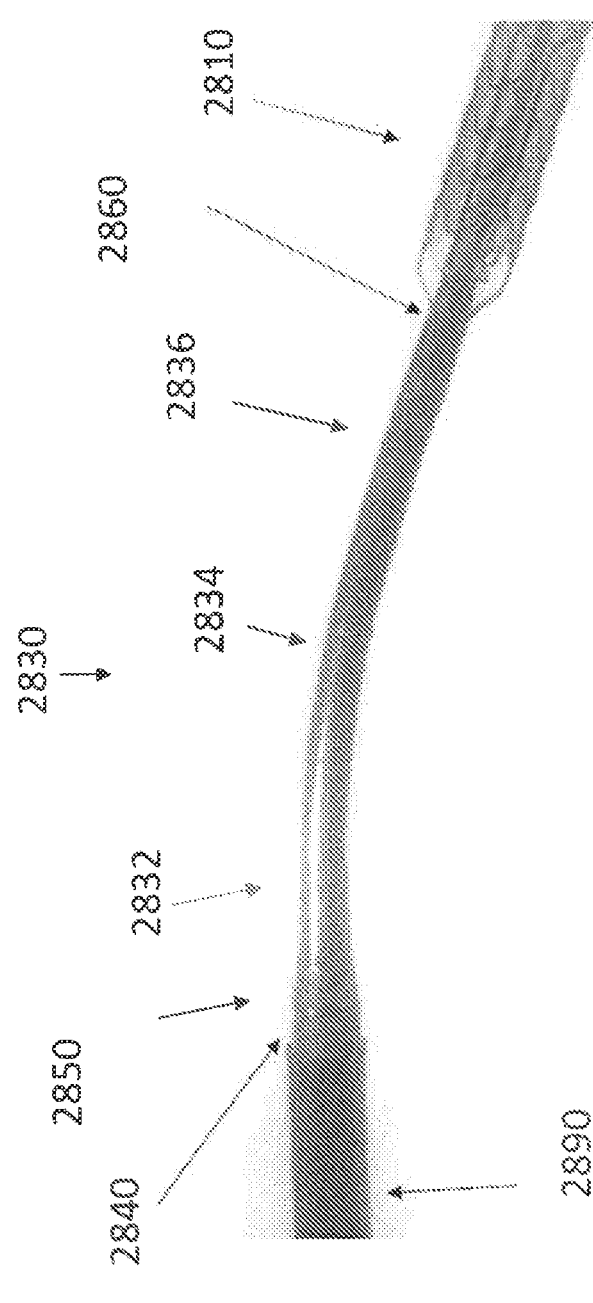

FIGS. 14B and 14D illustrate a distal end of catheter outer shaft 2840, which is shown coupled to a solid (not laser cut) proximal end of tubular member 2831 as shown. Sheath 2890, which is shown in a retracted position in FIG. 14D, is also shown. Sheath 2890 is adapted to be moved distally relative to the position shown (e.g., via actuation of a handle actuator) to facilitate collapse of pump portion 2810, which is in this non-limiting example is expandable and collapsible.

FIG. 14D further shows the blood pump in its entirety, including pump portion 2810 coupled to the elongate body. As shown and described herein, the elongate body can include a preferential bending region or zone 2830, which can be more flexible than other regions of the elongate body. For example, the elongate body may include proximal region 2850 and distal region 2860 that are more stiff (less flexible) than preferential bending zone 2830. Alternatively, the preferential bending zone 2830 can extend to be adjacent to or coupled of the pump portion 2810, such that there is not a stiffer distal section 2860 distal to the preferential bending zone. In this embodiment, the elongate body may include a relatively stiff proximal region 2850 and a very flexible preferential bending zone 2830 coupled directly to or adjacent to the pump portion 2810.

As further described above, the pump portion 2810 itself may have sections or regions of varying flexibility. For example, the pump portion 2810 may include only a single proximal impeller, but may include an expandable scaffold that includes a proximal region and distal region (regions "IR" described above) that are stiffer than a central region (region "CR" above). When coupled to the elongate body, the pump may then include, from a proximal to distal direction, an elongate body having a relatively stiff proximal section, a preferential bending zone (2830) adjacent to the proximal section that is very flexible, an optional distal section adjacent to the preferential bending zone with increased stiffness relative to the preferential bending zone, a proximal region of the blood pump that is stiff relative to the preferential bending zone and houses a proximal impeller, and a central region of the blood pump portion that is less stiff than the proximal or impeller region of the blood pump.

Figure 15:
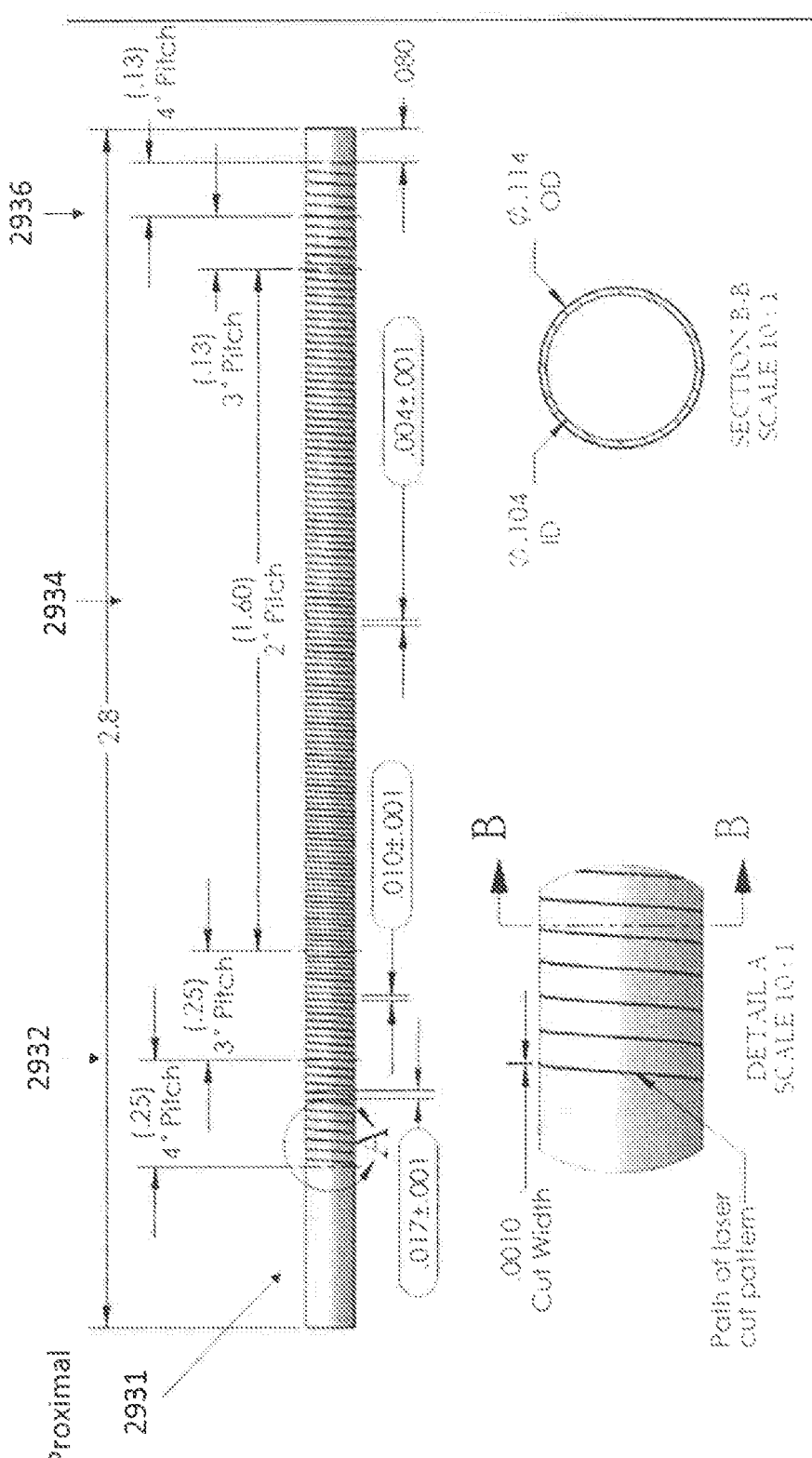
FIGS. 15 and 16 illustrate exemplary additional features of a tubular member that may have one or more gaps or cut formed therein.

Tubular member 2831 (and other similar tubular members) includes ends that are solid sections (not including one or more gaps or cuts formed therein), as is shown in FIGS. 14B, 14C and 15. The solid end sections may be solid so they are more easily coupled to or attached to one or more mating components in the proximal and distal stiffer regions 2850 and 2860. The solid end sections of tubular member 2831 may thus be considered to be disposed in the relatively stiffer proximal and distal regions 2850 and 2860 even though the are part of the tubular member that is part of the preferential bending zone.

Preferential bending region 2830 may in some examples comprises a tubular member 2831 that has a plurality of cuts or gaps formed therein, such as may be formed by laser cutting a tube. In some instances, preferential bending zone 2830 includes a stainless steel (or other suitable material) tubular member 2831. In instances in which the preferential bending zone includes tubular member with a plurality of gaps or cuts formed therein, the tubular member 2831 may be described as having a pattern formed therein.

In some examples, the pattern of tubular member 2831 may be uniform or non-varying over the length of preferential bending zone 2830. The flexibility of the tubular member may optionally be constant along its length.

In some embodiments, the tubular member 2831 may partially comprise or include a rigid or semi-rigid material formed into a braided pattern to provide a balance between flexibility and strength. For example, the tubular member 2831 can include a braided pattern of stainless steel encapsulated in an elastomer such as Pebax. The braided pattern can comprise, for example, a braid of a plurality of wires (e.g., 5 wires). The braided pattern can enable the tubular member, and thus the preferential bending region the flexibility and torque required of the blood pump while also providing resistance to collapse. The torquability of the braided pattern also reacts well to twisting, which can be an advantage during delivery and placement of the blood pump.

In some embodiments, however, the pattern of member 2831 may vary over its length, and the varying pattern may contribute to varying flexibility of the tubular member 2831 over at least a portion of its length, including varying flexibility over the length of the preferential bending zone. The pattern may vary in one or more of size (axial and/or circumferential) of the gap(s), pitch of the cut, etc., continuity/discontinuities of the cut, the varying of which may be known in general for controlling flexibility in a laser cut tubular material.

Gaps, cuts, or braided patterns formed in tubular member 2831 may be continuous along its length, or there may be one or more discontinuities in the gaps or cuts along its length. Discontinuities in cuts may be incorporated to contribute to a desired flexibility, including varying the flexibility along its length.

In some examples, it may beneficial for the preferential bending zone to a varying flexibility along at least a portion of its length. For example, it may be undesirable to have too abrupt of a change in flexibility between a distal end of catheter shaft 2840 and/or proximal region 2850 and a region within the preferential bending zone with a desired greatest amount of flexibility. For example, abrupt changes in flexibility may increase the likelihood of kinking at the transition. For blood pumps that include a rotating drive assembly through the catheter and to the pump portion, kinking may cause the rotating drive assembly to hit the outer structure of there is kinking. It is thus generally desirable to have smooth bend along the length of the catheter/sheath and through the preferential bending zone. To avoid kinking, it may thus be beneficial for the preferential bending zone to include and create a transition in flexibility from the catheter shaft distal end and a most flexible region of the preferential bending zone. For example only, proximal region 2832 of preferential bending zone 2830 may be less flexible than central region 2834 of preferential bending zone 2830, but more flexible than first region 2850 that is adjacent to preferential bending zone 2830, wherein proximal region 2832 may function at least partially as a flexibility transition zone between proximal region 2850 and central region 2834 of the preferential bending zone 2830. Any of the individual regions herein may themselves have varying flexibility along at least a portion of their lengths. Additional examples of transition regions are set forth below.

In mere examples, proximal region 2832 of preferential bending zone 2830 may have a pattern with smaller gaps and/or a larger pitch that in central region 2834, which may impart greater stiffness to proximal region 2832 compared to central region 2834. Central region 2834 may have larger gaps and/or a smaller pitch than proximal region 2832. Other techniques may be used to impart less flexibility in proximal/transition region 2832 than in central region 2834 so that proximal region 2832 acts as a flexibility transition region and prevents kinking at the transition between the catheter shaft 2840 and the preferential bending zone 2830.

This examples illustrates optional distal region 2836 of the preferential bending zone 2830, which may have the same flexibility as central region 2834 or may have a decreased flexibility relative to central region 2834. For example, a distal region 2836 may also function as a flexibility transition between central region 2834 and distal stiffer region 2860 that is distal to the preferential bending region 2830. Distal region 2836 may have less relative flexibility similar to proximal region 2832 and may also provide a flexibility transition region to avoid kinking.

Other known techniques using gap variation in the pattern to create desired flexibility may be utilized in any of the preferential bending zones herein, including variations to create any of the one or more flexibility transitions zones herein.

As is set forth above, distal region 2860 may be stiffer than preferential bending zone 2830, which may be due in part to a bearing housing and a general coupling between the pump portion 2810 and the donate body. As shown in exemplary FIG. 14C, distal region 2860 may include a relatively stiff tube 2861 (e.g., a hypotube) that is secured to a solid distal end section of tubular member 2831, as shown. First region 2860 may include one or more bearings 2862, mere examples of which are illustrated in FIG. 14C. The distal end of tubular member 2831 may be considered part of distal stiffer region 2860.

Proximal region 2850 of the elongate body is proximal to and has a greater stiffness (less flex) than preferential bending zone 2830, the stiffness of which may be at least partly caused by one or more of a catheter shaft, coupling component(s) between catheter and preferential bending zone 2830 or a drive cable tube disposed within the catheter shaft 2840, or a distal end of a sheath.

Figure 14E:
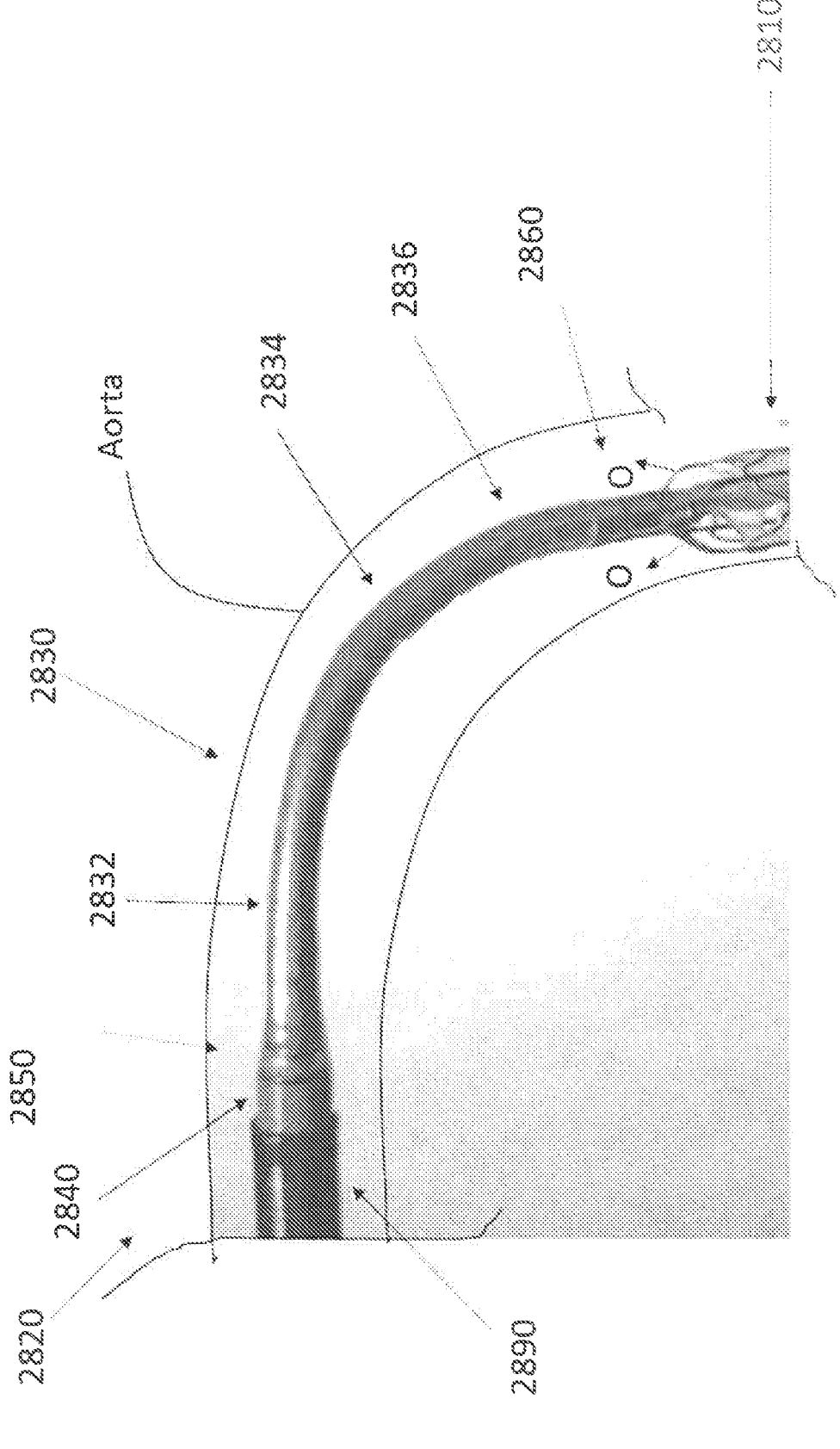
Figure 14F:
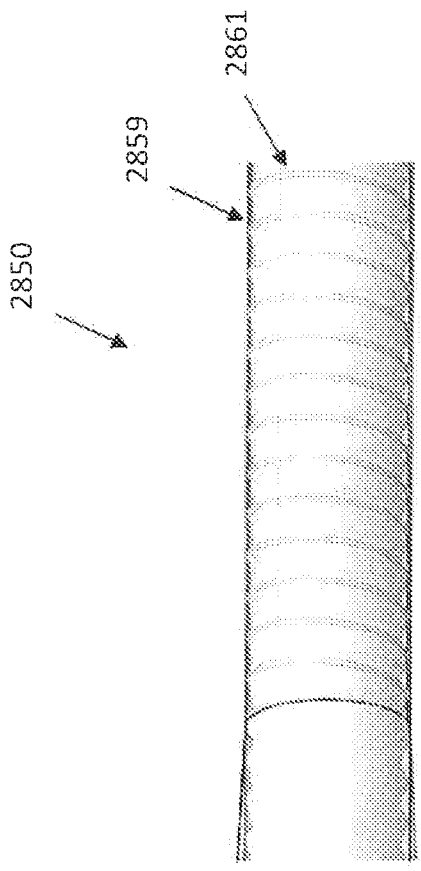

FIG. 14F is a close-up view of the proximal region 2850 providing a view of braided pattern 2859 (as described above) and axial strengthening member(s) 2861. As described above, braided pattern 2859 can be configured to provide a balance between flexibility and strength in the portion of the blood pump proximal to the outflow region. It should be understood that while the features of FIG. 14F are described as residing within the proximal region 2850, these features, including the braided pattern 2859 and the axial strengthening member 2861 can reside in the proximal region 2850, the preferential bending region 2831, and/or the distal region 2860. In some embodiments, the braided pattern can comprise stainless steel encapsulated in an elastomer such as Pebax. The braided pattern can comprise, for example, a braid of a plurality of wires (e.g., 5 wires). The braided pattern can enable proximal region, the preferential bending region, and/or the distal region the flexibility and torque required of the blood pump while also providing resistance to collapse. The torquability of the braided pattern also reacts well to twisting, which can be an advantage during delivery and placement of the blood pump.

Additionally the axial strengthening member 2861 can run axially along a length of the blood pump, including along some or all portions of the proximal portion, the preferential bending region, and/or the distal region. In some embodiments, the axial strengthening member 2861 comprises one or more strands of a rigid or or semi-rigid material such as kevlar. While only one axially extending axial strengthening member is shown in FIG. 14F, it should be understood that multiples can be implemented in other embodiments, including axial strengthening members positioned at various points around a circumference of the proximal region, preferential region, and/or distal region. The axial strengthening member can be configured to provide tensile elements which can assist in sheathing or deploying the blood pump. In some embodiments, the proximal region, the preferential bending region, and/or the distal region can comprise the braided pattern and/or the axial strengthening member(s) positioned between one or more urethane liners or layers (such as Pebax), such that the braded pattern and/or axial strengthening member(s) are encapsulated in urethane.

In some examples, tubular member 2831 in the preferential bending zone 2830 has gaps, slots or cuts formed therein, and may also serve as an outer layer of a fluid pathway "F" as shown in FIG. 14B and 14C. For example, fluid pathway F may comprises any of the purge and/or lubrication fluid pathways herein, which may help cool and/or lubricate pump bearings and/or prevent blood from entering into internal areas of the elongate body.

In embodiments in which the laser cut tubular material 2831 forms part of a fluid pathway, the preferential bending zone may include one or more coating layers of material 2832 (see FIG. 14B) disposed about the tubular material, such as, without limitation, a nylon coating member, which may provide an outer barrier or seal for the outer fluid pathway F along the length of tubular member 2831. In some embodiments, coating 2832 may include a thin walled Pebax layer of material. The covering or coating 2832 may, depending on the manufacturing of the preferential bending zone, tend to fill in the voids of the gaps formed in tubular material 2831, which may add some structural support to the preferential bending zone in the regions of the one or more gaps (compared to a lack of a coating or covering). The material of the coating may impact the overall flexibility of the preferential bending zone, and may thus need to be considered depending on the desired properties of the flexible bending zone.

The preferential bending zones herein are proximal to the pump portions, and when a sheath is used to collapse collapsible pump portion, the sheath is advanced over the preferential bending zone. For example, sheath 2890 in FIG. 14D can be distally advanced to collapse pump portion 2810. As the sheath is advanced distally, the sheath may apply a force on the outflow struts of the pump portion, which are shown in FIGS. 14A, 14D, and 14E. Force on the outflow struts may cause tension in the preferential bending zone because the preferential bending zone is coupled (indirectly) to the pump portion. The pattern of the preferential bending zone may thus at least partly contribute to the desired flexibility to bend preferentially and absorb forces as described herein, as well as be able to accept the tension forces during the sheathing process.

In some embodiments the preferential bending zone has a length that allows it to preferentially bend along a particular region of an aorta to be able to absorb forces and minimize the amount of forces that are translated distally to the pump portion. FIG. 14E illustrates an exemplary pump portion 2810 positioned across an aortic valve (not shown for clarity), wherein an outflow "O" is positioned in an ascending aorta. Elongate body 2820 extends through the curved aorta as shown. As can be seen, a region in the elongate body at the top of the arch is at an angle relative to a long axis of the pump when the pump is placed across the valve, optionally as much as 90 degrees or more. Without a preferential bending region proximal to the pump portion, the bending of the catheter and shaft in the aorta may create bending forces on the pump portion that may increase the likelihood of the blood conduit axis becoming dis-aligned with an impeller long axis at the location of the impeller. Exemplary preferential bending zone 2830 is more flexible that adjacent regions of the catheter blood pump and more easily assumes a bent configuration in the region of the catheter pump between the pump portion and the catheter shaft and sheath that are further proximally in the aorta.

The preferential bending zones herein may have a length so as to preferentially bend in the anatomical region of the aorta when the pump portion is placed across a valve. In some examples, the preferential bending zones herein may be from 0.5 inch to 7 inches, such 0.5 inches to 5 inches, such as 1 inch to 4 inches long, such as 3-4 inches long. In some examples, a proximal transition region (e.g., 2832, 2932) may be between 0.20 inches and 3 inches, and may provide a transition in flexibility as set forth above. In some embodiments a relatively more flexible central region 2834, 2934 of the preferential bending zone is from 0.5 inches to 4 inches, such as 0.5 inches to 3 inches. Relatively more stiff distal region, such as region 2836 or 2936, may optionally be from 0.5 inches to 2 inches, such as 0.1 inches to 1 inch. In other examples the preferential bending zone may be longer, and may have a length so that it extends along substantially all of the aortic arch when the sheath is retracted.

Any of the methods of use herein (including methods of deploying a pump portion) may be incorporated in methods of deploying a pump portion of a catheter blood pump that includes a preferential bending region.

As set forth herein, preferential bending zones may include tubular members with cuts or gaps formed therein. The gaps therethrough may provide the preferential bending zone with more rotational freedom than adjacent elongate body regions. Adjacent sections may be tubular or more tubular, without cuts or gaps formed therein. The relative greater rotational freedom may, without wishing to be bound by any particular theory, optionally help the pump portion be seated or positioned across the valve while receiving fewer forces in response to the bend formed in the elongate body when following the curvature of the aorta. Additionally, some rotational freedom imparted to the preferential bending zone may provide other advantages such as less stress on proximal outflow struts, for example without limitation.

As shown in FIG. 14B, a drive cable (e.g., drive cable 2880) extends through the catheter and the preferential bending zone, and is rotationally coupled to one or more impellers in the pump portion. As set forth, there are advantages to providing smooth bends along the device and avoiding kinking.

One aspect of the disclosure includes methods of deploying a pump portion of a catheter blood pump across an aortic valve and positioning a preferential bending zone of an elongate body in the ascending aorta. These methods may include positioning the preferential bending region in a location of the ascending aorta so as to cause the preferential bending region to assume a more curved configuration than proximal and distal adjacent regions of the elongate body, while reducing deflection forces that are translated to the pump portion, an example of which is shown in 14E.

Figure 16:
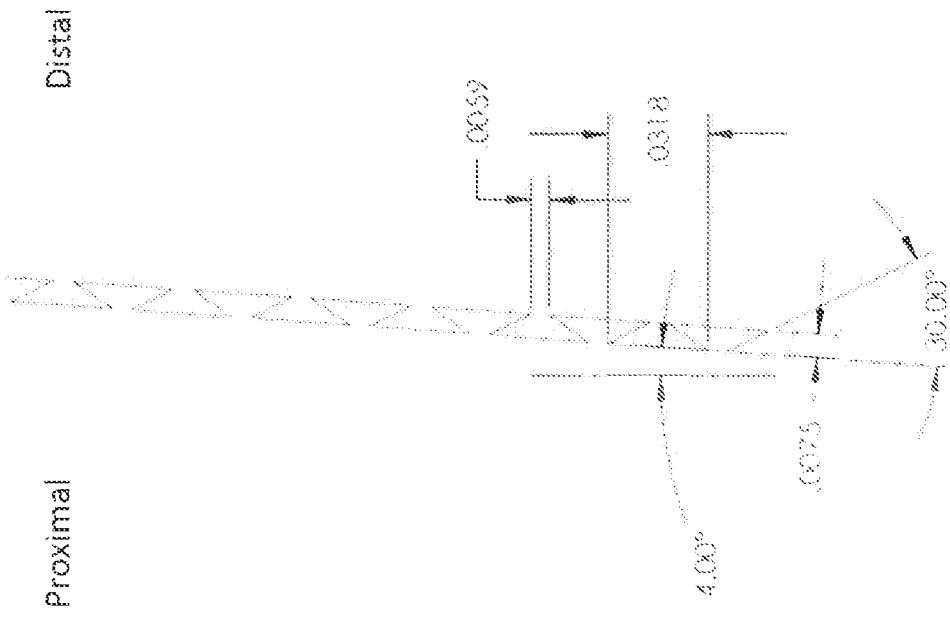

FIGS. 15 and 16 illustrate exemplary additional features of a tubular member that may have one or more gaps or cut formed therein, such as by laser cutting. The tubular member shown in FIGS. 15 and 16 may be similar to tubular member 2831 shown and described herein. FIG. 15 generally shows tubular member 2931, including solid end sections without cuts formed therein, which are described above to ease the coupling of the tubular member to adjacent structures. In this merely exemplary embodiment, the preferential bending zone includes a plurality of discrete zones have flexibility different than that of adjacent zones, and in particular includes five zones of varying flexibility, as shown.

In some applications it may be desirable for the preferential bending zone to be as close as possible to the pump portion. Distal region 2860 (and other similar distal regions) may, however, be relatively stiff due to one or more of bearing components and/or coupling components. To position the most flexible part of the preferential bending zone as close to the pump portion as possible (if that is in fact desired), the distal flexibility transition region of the preferential bending zone may have a length that is less than a flexibility transition zone in a proximal region of the preferential bending zone, where it may not be as necessary or even desired to have a flexibility transition zone that is as short as the distal flexibility transition zone. For example, it may be generally more desirable for transition zones to be long enough to provide a smooth transition and avoid kinking. It may thus be desirable that the proximal flexibility transition zone have length to provide a transition region, but the distal flexibility transition zone is shorter to position the most flexible part of the preferred bending zone as close as possible to the pump portion.

FIG. 15 illustrates an exemplary tubular member by itself (other catheter blood pump parts not shown) having solid ends, and a laser cut pattern therebetween, as shown. The laser cut pattern can be incorporated into any of the preferential bending regions of the elongate body herein. Preferential bending zone includes central region 2934, which has the greatest flexibility, and which may be similar to central region 2834, and may include any suitable features thereof. Preferential bending zone includes distal flexibility transition region 2936, which provides a flexibility transition between central region 2934 and the solid distal end (which may be coupled to one or more components in the distal relatively stiffer region (e.g., coupling and/or bearing housing component(s)). Preferential bending zone includes proximal flexibility transition region 2932, which provides a flexibility transition zone between most flexible central region 2934 and the solid proximal end of tubular member (which may be coupled to one or more components in the proximal relatively stiffer region of the elongate body (e.g., catheter shaft).

In this merely exemplary embodiment, distal transition zone 2936 includes a plurality of sections (two in this embodiment, as shown) having different flexibilities, and proximal transition region 2932 includes a plurality of sections (two in this embodiment, as shown) having different flexibilities.

As shown, distal transition region 2936 is shorter than proximal transition region 2932, which allows the most flexible central region 2934 to be as close to the pump portion as possible, and allows the transition region 2932 to be longer to impart a longer transition region.

The lengths shown in FIG. 15 (which are in inches) are merely illustrative and not in any way limiting. Exemplary ranges of lengths of the different zones are described above.

In the example of FIG. 15, the different flexibilities in the different zones of the preferential bending region may be at least partly dependent on the pitch of the cut formed therein, as shown. For example, the transition regions 2932 and 2936 may generally have a gap with a greater pitch than the gap in central region 2934, wherein the smaller pitch in the central region may contribute to the relatively greater flexibility. Additionally, as shown, the transition regions may include a plurality of sections having different pitches, which may help create a more gradual variation in flexibility in the transition regions.

In some examples the pattern of the cut may be the same along the preferential bending zone, but the pitch may vary to impart the desired flexibilities.

Also, as shown in exemplary FIG. 15, the solid distal end region of the tubular member is shorter than the solid proximal end section of the tubular member.

Relying on a laser cut tubular member concept to create and impart desired flexibilities along the length of the preferential bending region may allow for more fine tuning and control of the flexibility at any given location or section than if relying on varying the durometer of a polymeric material, for example.

FIG. 16 illustrates a merely exemplary cut pattern for any of the tubular members, and illustrates merely exemplary dimensions, angles and pitches. The pattern shown in FIG. 16 may extend along any or all of the length of the preferential bending zone. For example, the pattern and section shown in FIG. 16 may be in detail A from FIG. 15, which is within proximal transition region 2932 (and which is also in a proximal region of proximal transition region 2932).

What is claimed is:

1. A catheter blood pump, comprising:
   a pump portion comprising a blood impermeable conduit extending between an inflow and an outflow, and an impeller disposed at least partially within the blood impermeable conduit;
   an elongate body coupled to and extending proximally from the pump portion and being disposed proximal to the outflow and blood impermeable conduit of the pump portion, wherein a distal region of the elongate body includes a preferential bending region that is more flexible than a first region of the elongate body adjacent to and proximal to the preferential bending region and more flexible than a second region of the elongate body adjacent to and distal to the preferential bending region, the second region adjacent to and proximal to the outflow of the pump.

2. The blood pump of claim 1, wherein the preferential bending region is more flexible than the outflow region of the pump portion.

3. The blood pump of claim 1, wherein the preferential bending region includes at least one of material or structure that contributes at least partially to the relatively greater flexibility in the preferential bending region.

4. The blood pump of claim 1, wherein the preferential bending region has a flexibility such that when the pump portion is positioned across an aortic valve, the preferential bending region assumes a bent configuration in an ascending aorta so as to maintain as co-linear an impeller long axis and a blood impermeable conduit long axis at the location of the impeller.

5. The blood pump of claim 4, wherein a proximal end of the impeller, including a blade, is only partially covered by the blood impermeable conduit.

6. The blood pump of claim 1, wherein the first region includes a distal end of an elongate outer catheter shaft.

7. The blood pump of claim 1, wherein the first region includes a distal end of drive cable tube, the drive cable tube extending around a drive cable.

8. The blood pump of claim 7, wherein the first region includes a distal end of the drive cable tube.

9. The blood pump of claim 1, wherein the first region includes a clean fluid path and a fluid return pathway.

10. The blood pump of claim 1, wherein the preferential bending region includes a clean fluid pathway.

11. The blood pump of claim 1, wherein the second region comprises a bearing housing that houses at least one bearing.

12. The blood pump of claim 11, wherein the bearing housing is a proximal bearing housing, the catheter blood pump further comprising a distal bearing housing disposed distal to a distal end of the blood conduit.

13. The blood pump of claim 1, wherein the second region that is distal to the preferential bending region comprises a rigid cylindrical member disposed about a bearing.

14. The blood pump of claim 1, wherein the preferential bending region has a length from 0.5 inches to 7 inches, optionally from 1 inch-5 inches.

15. The blood pump of claim 1, wherein the preferential bending region comprises a flexible tubular member with a plurality of gaps formed through the flexible tubular member, the plurality of gaps at least partially contributing to the flexibility of the flexible region.

16. The blood pump of claim 15, wherein the plurality of gaps are part of a continuous gap formed in the flexible tubular member.

17. The blood pump of claim 16, wherein the continuous gap includes at least a section with a helical configuration.

18. The blood pump of claim 16, wherein the plurality of gaps are formed by a plurality of interlocking structural elements.

19. The blood pump of claim 18, wherein the plurality of interlocking structural elements are spaced so as to allow for some axial movement therebetween and further prevent axial movement therebetween beyond a certain amount.

20. The blood pump of claim 1, wherein the plurality of interlocking structural elements are spaced so as to allow for some rotational movement therebetween and further prevent circumferential movement therebetween beyond a certain amount.

21. The blood pump of claim 1, wherein the blood pump is sized and configured to be inserted into a heart of a subject, and wherein the preferential bending region is configured to extend at least partially along an aortic arch of the subject when the pump portion is positioned across an aortic valve of the subject.

\* \* \* \* \*